(12) United States Patent  
Watanabe et al.

(10) Patent No.: US 7,799,030 B2  
(45) Date of Patent: Sep. 21, 2010

(54) ORTHOPAEDIC PLATE AND SCREW ASSEMBLY

(75) Inventors: Kohsuke Watanabe, Memphis, TN (US); Joseph M. Ferrante, Bartlett, TN (US); Keith McReynolds, Olive Branch, MS (US)

(73) Assignee: Smith & Nephew, Inc., Memphis, TN (US)

( * ) Notice: Subject to any disclaimer, the term of this patent is extended or adjusted under 35 U.S.C. 154(b) by 778 days.

(21) Appl. No.: 11/725,872

(22) Filed: Mar. 20, 2007

(65) Prior Publication Data

US 2007/0270845 A1    Nov. 22, 2007

Related U.S. Application Data

(63) Continuation-in-part of application No. 10/937,075, filed on Sep. 8, 2004, now Pat. No. 7,534,244, which is a continuation of application No. 10/658,351, filed on Sep. 8, 2003, now abandoned.

(60) Provisional application No. 60/783,931, filed on Mar. 20, 2006.

(51) Int. Cl.
*A61B 17/56*    (2006.01)

(52) U.S. Cl. .............................. 606/62; 606/64; 606/304

(58) Field of Classification Search ................... 606/62, 606/63, 64, 65, 66, 67, 68, 304, 310  
See application file for complete search history.

(56) References Cited

U.S. PATENT DOCUMENTS

| | | | |
|---|---|---|---|
| 2,267,925 A | 12/1941 | Johnston | |
| 2,699,774 A | 1/1955 | Harrison | |

(Continued)

FOREIGN PATENT DOCUMENTS

AU    199728574    9/1997

(Continued)

OTHER PUBLICATIONS

Brochure entitled "OR manual PLATON (tantum))) the medical people," 22 pages, Aug. 2002.

(Continued)

*Primary Examiner*—Pedro Philogene  
(74) *Attorney, Agent, or Firm*—Fish & Richardson P.C.

(57) ABSTRACT

Systems, devices and methods are disclosed for treating fractures and other bone maladies. The systems, devices and methods may include one or both of a stabilizing structure, such as an implant, bone plate, or other device and a fastening assembly, such as a lag screw and compression screw assembly. The stabilizing structure in some embodiments has a proximal section with a transverse aperture and a cross-section that may be shaped to more accurately conform to the anatomical shape of cortical bone and to provide additional strength and robustness in its lateral portions, preferably without requiring significant additional material. The fastening assembly may be received to slide, in a controlled way, in the transverse aperture of the stabilizing structure. In some embodiments, the engaging member and the compression member are configured so that the compression member interacts at least indirectly with the stabilizing structure and a portion of the engaging member to enable controlled movement between the first and second bone fragments. This configuration is useful for, among other things, compressing a fracture.

13 Claims, 31 Drawing Sheets

U.S. PATENT DOCUMENTS

| | | | |
|---|---|---|---|
| 3,374,786 A | 3/1968 | Callender | |
| 3,530,854 A * | 9/1970 | Kearney | 606/67 |
| 3,630,261 A | 12/1971 | Gley | |
| 4,103,683 A | 8/1978 | Neufeld | |
| 4,172,452 A | 10/1979 | Forte | |
| 4,432,358 A | 2/1984 | Fixel | |
| 4,438,762 A | 3/1984 | Kyle | |
| 4,484,570 A | 11/1984 | Sutter et al. | |
| 4,612,920 A | 9/1986 | Lower | |
| 4,621,629 A | 11/1986 | Koeneman | |
| 4,622,959 A | 11/1986 | Marcus | |
| 4,641,640 A | 2/1987 | Griggs | |
| 4,657,001 A * | 4/1987 | Fixel | 606/66 |
| 4,776,330 A | 10/1988 | Chapman et al. | |
| 4,827,917 A | 5/1989 | Brumfield | |
| 4,978,349 A | 12/1990 | Frigg | |
| 5,007,910 A | 4/1991 | Anapliotis et al. | |
| 5,032,125 A | 7/1991 | Durham et al. | |
| 5,041,114 A | 8/1991 | Chapman et al. | |
| 5,041,116 A | 8/1991 | Wilson | |
| 5,100,404 A | 3/1992 | Hayes | |
| 5,112,333 A | 5/1992 | Fixel | |
| 5,122,141 A | 6/1992 | Simpson et al. | |
| 5,167,663 A | 12/1992 | Brumfield | |
| 5,176,681 A | 1/1993 | Lawes et al. | |
| 5,190,544 A | 3/1993 | Chapman et al. | |
| 5,269,784 A | 12/1993 | Mast | |
| 5,312,406 A | 5/1994 | Brumfield | |
| 5,324,292 A | 6/1994 | Meyers | |
| 5,364,398 A | 11/1994 | Chapman et al. | |
| 5,429,640 A | 7/1995 | Shuler et al. | |
| 5,429,641 A | 7/1995 | Gotfried | |
| 5,454,813 A | 10/1995 | Lawes | |
| 5,514,137 A | 5/1996 | Coutts | |
| 5,514,138 A | 5/1996 | McCarthy | |
| 5,531,748 A | 7/1996 | De la Caffiniere | |
| 5,562,666 A | 10/1996 | Brumfield | |
| 5,562,667 A | 10/1996 | Shuler et al. | |
| 5,573,536 A | 11/1996 | Grosse et al. | |
| 5,591,168 A | 1/1997 | Judet et al. | |
| 5,653,709 A | 8/1997 | Frigg | |
| 5,658,288 A | 8/1997 | Kim | |
| 5,690,640 A | 11/1997 | Gotfried | |
| 5,713,902 A | 2/1998 | Friedl | |
| 5,741,256 A | 4/1998 | Bresina | |
| 5,743,908 A | 4/1998 | Kim | |
| 5,743,912 A | 4/1998 | Lahille et al. | |
| 5,749,872 A | 5/1998 | Clewett et al. | |
| 5,772,662 A | 6/1998 | Chapman et al. | |
| 5,779,704 A | 7/1998 | Kim | |
| 5,810,821 A | 9/1998 | Vandewalle | |
| 5,908,422 A | 6/1999 | Bresina | |
| 5,928,235 A | 7/1999 | Friedl | |
| 5,954,722 A | 9/1999 | Bono | |
| 5,984,970 A | 11/1999 | Bramlet | |
| 6,059,786 A | 5/2000 | Jackson | |
| 6,077,264 A | 6/2000 | Chemello | |
| 6,102,913 A | 8/2000 | Jackson | |
| 6,106,528 A | 8/2000 | Durham et al. | |
| 6,123,708 A | 9/2000 | Kilpela et al. | |
| 6,126,661 A | 10/2000 | Faccioli et al. | |
| 6,139,552 A | 10/2000 | Horiuchi | |
| 6,183,474 B1 | 2/2001 | Bramlet et al. | |
| 6,187,007 B1 | 2/2001 | Frigg et al. | |
| 6,221,074 B1 | 4/2001 | Cole et al. | |
| 6,228,086 B1 | 5/2001 | Wahl et al. | |
| 6,235,031 B1 | 5/2001 | Hodgeman et al. | |
| 6,235,033 B1 | 5/2001 | Brace et al. | |
| 6,261,290 B1 * | 7/2001 | Friedl | 606/64 |
| 6,270,499 B1 | 8/2001 | Leu et al. | |
| 6,322,591 B1 | 11/2001 | Ahrens | |
| 6,406,477 B1 | 6/2002 | Fujiwara | |
| 6,409,768 B1 | 6/2002 | Tepic et al. | |
| 6,423,066 B1 | 7/2002 | Harder et al. | |
| 6,443,954 B1 * | 9/2002 | Bramlet et al. | 606/62 |
| 6,461,360 B1 | 10/2002 | Adam | |
| 6,468,278 B1 | 10/2002 | Muckter | |
| 6,475,242 B1 | 11/2002 | Bramlet | |
| 6,511,481 B2 | 1/2003 | von Hoffmann et al. | |
| 6,524,314 B1 | 2/2003 | Dean et al. | |
| 6,533,789 B1 | 3/2003 | Hall, IV et al. | |
| 6,562,042 B2 | 5/2003 | Nelson | |
| 6,565,573 B1 | 5/2003 | Ferrante | |
| 6,569,165 B2 | 5/2003 | Wahl et al. | |
| 6,575,975 B2 | 6/2003 | Brace et al. | |
| 6,645,209 B2 | 11/2003 | Hall et al. | |
| 6,648,889 B2 | 11/2003 | Bramlet et al. | |
| 6,652,529 B2 | 11/2003 | Swanson | |
| 6,695,844 B2 | 2/2004 | Bramlet et al. | |
| 6,719,759 B2 | 4/2004 | Wagner | |
| 6,755,832 B2 | 6/2004 | Happonen | |
| 6,902,567 B2 | 6/2005 | Del Medico | |
| 6,905,500 B2 | 6/2005 | Jeon et al. | |
| 6,932,818 B2 | 8/2005 | Behrens | |
| 6,932,819 B2 | 8/2005 | Wahl et al. | |
| 7,135,023 B2 * | 11/2006 | Watkins et al. | 606/65 |
| 7,503,919 B2 | 3/2009 | Shaw | |
| 2001/0012939 A1 | 8/2001 | Wahl et al. | |
| 2001/0037112 A1 | 11/2001 | Brace et al. | |
| 2002/0032445 A1 | 3/2002 | Fujiwara | |
| 2002/0099379 A1 | 7/2002 | Adam | |
| 2002/0107578 A1 | 8/2002 | Speitling et al. | |
| 2002/0111629 A1 | 8/2002 | Phillips | |
| 2002/0133156 A1 | 9/2002 | Cole | |
| 2002/0143334 A1 | 10/2002 | Hoffmann et al. | |
| 2002/0156473 A1 | 10/2002 | Bramlet et al. | |
| 2003/0004514 A1 | 1/2003 | Frigg et al. | |
| 2003/0069582 A1 | 4/2003 | Culber | |
| 2003/0074000 A1 | 4/2003 | Roth et al. | |
| 2003/0114855 A1 | 6/2003 | Wahl et al. | |
| 2003/0195515 A1 | 10/2003 | Sohngen | |
| 2004/0010255 A1 | 1/2004 | Warburton | |
| 2004/0127898 A1 | 7/2004 | Adam | |
| 2005/0010223 A1 | 1/2005 | Gotfried | |
| 2005/0055024 A1 | 3/2005 | James et al. | |
| 2005/0069397 A1 | 3/2005 | Shavit et al. | |
| 2005/0070902 A1 | 3/2005 | Medoff | |
| 2005/0101959 A1 | 5/2005 | Mitkovic | |
| 2005/0131411 A1 | 6/2005 | Culbert | |
| 2005/0143739 A1 | 6/2005 | Shinjo et al. | |
| 2005/0149024 A1 | 7/2005 | Ferrante | |
| 2005/0149025 A1 | 7/2005 | Ferrante | |
| 2005/0177158 A1 | 8/2005 | Doubler et al. | |
| 2005/0234457 A1 | 10/2005 | James et al. | |
| 2005/0273103 A1 | 12/2005 | Wahl et al. | |
| 2006/0036248 A1 | 2/2006 | Ferrante et al. | |
| 2006/0069392 A1 | 3/2006 | Renzi Brivio et al. | |
| 2006/0084999 A1 | 4/2006 | Aschmann | |
| 2006/0106384 A1 | 5/2006 | Reber et al. | |
| 2006/0106385 A1 | 5/2006 | Pennig | |
| 2006/0149247 A1 | 7/2006 | Frigg et al. | |
| 2007/0162011 A1 | 7/2007 | Leyden et al. | |
| 2007/0288017 A1 | 12/2007 | Kaup | |
| 2007/0299447 A1 | 12/2007 | Watanabe | |
| 2008/0004623 A1 | 1/2008 | Ferrante | |
| 2008/0033430 A1 | 2/2008 | Ferrante et al. | |
| 2008/0051790 A1 | 2/2008 | Defossez | |
| 2008/0119855 A1 | 5/2008 | Hoegerle et al. | |
| 2008/0119856 A1 | 5/2008 | Gotfried | |
| 2008/0188853 A1 | 8/2008 | Ferrante et al. | |
| 2008/0195098 A1 | 8/2008 | Gotfried | |
| 2008/0269752 A1 | 10/2008 | Simon et al. | |

| | | |
|---|---|---|
| 2009/0088768 A1 | 4/2009 | Grant et al. |

FOREIGN PATENT DOCUMENTS

| | | |
|---|---|---|
| AU | 200032139 | 8/2000 |
| AU | 2006252075 | 7/2007 |
| AU | 2008201469 | 10/2008 |
| BE | 551 875 | 11/1956 |
| DE | 29811670 | 9/1998 |
| DE | 197 23 339 C2 | 12/1998 |
| DE | 198 29 228 C | 10/1999 |
| EP | 0257118 | 3/1988 |
| EP | 0321170 | 6/1989 |
| EP | 0 355 411 A1 | 2/1990 |
| EP | 0441 577 A2 | 8/1991 |
| EP | 0 551 846 A1 | 7/1993 |
| EP | 586 824 | 3/1994 |
| EP | 0 640 318 A1 | 3/1995 |
| EP | 0 486 483 B1 | 2/1996 |
| EP | 0 853 923 B1 | 7/1996 |
| EP | 0 838 199 A1 | 4/1998 |
| EP | 0617927 | 1/1999 |
| EP | 0968685 | 1/2000 |
| EP | 1024762 | 8/2000 |
| EP | 00715832 B1 | 1/2002 |
| EP | 01175872 A2 | 1/2002 |
| EP | 1 273 271 A2 | 6/2002 |
| EP | 1267734 | 2/2003 |
| EP | 1416868 | 5/2004 |
| EP | 1974682 | 10/2008 |
| FR | 2718013 | 10/1995 |
| FR | 2841459 | 1/2004 |
| FR | 2 873 913 | 2/2006 |
| GB | 2209947 | 6/1989 |
| JP | 2021859 | 1/1990 |
| JP | 09 066061 | 3/1997 |
| JP | 9066060 | 3/1997 |
| JP | 10323351 | 12/1998 |
| JP | 2002 065687 | 3/2002 |
| JP | 2003 038508 | 2/2003 |
| JP | 2004089259 | 3/2004 |
| WO | WO 95/26688 | 10/1995 |
| WO | WO 97/08999 | 3/1997 |
| WO | WO 97/18769 | 5/1997 |
| WO | WO 97/37606 | 10/1997 |
| WO | WO 98/02105 | 1/1998 |
| WO | WO 00/76414 A1 | 12/2000 |
| WO | WO 01/34045 A1 | 5/2001 |
| WO | WO 01/39679 A1 | 7/2001 |
| WO | WO 01/56487 | 8/2001 |
| WO | WO 01/56487 A1 | 8/2001 |
| WO | WO 0178615 A1 | 10/2001 |
| WO | WO 01/91660 | 12/2001 |
| WO | WO 02/078555 A1 | 10/2002 |
| WO | WO 02/085219 | 10/2002 |
| WO | WO 02/085228 A1 | 10/2002 |
| WO | WO 03/015649 A1 | 2/2003 |
| WO | WO 03/022166 A1 | 3/2003 |
| WO | WO 03/028567 | 4/2003 |
| WO | WO 2004032726 A2 | 4/2004 |
| WO | WO 2004/110292 | 12/2004 |
| WO | WO 2005/025436 | 3/2005 |
| WO | WO 2005/025437 | 3/2005 |
| WO | WO 2005/034794 A2 | 4/2005 |
| WO | WO 2006/007553 A2 | 1/2006 |
| WO | WO 2006/040612 | 4/2006 |
| WO | WO2006092583 A1 | 9/2006 |
| WO | WO 2007/038560 A1 | 4/2007 |
| WO | WO 2007/109302 | 9/2007 |
| WO | WO 2008/022136 | 2/2008 |
| WO | WO 2008098728 A2 | 8/2008 |
| WO | WO 2008/128663 | 10/2008 |

OTHER PUBLICATIONS

Web page entitled, The PLATON-Locking-Nail system, numerous improvements, * one page, Dec. 6, 2003.

Web page entitled The PLATON-Locking-Nail system: Quality without compromise, two pages, Jun. 30, 2003.

Ballabarba, et al., Percutaneous Treatment of Peritrochanteric Fractures Using the Gamma Nail, *Clin. Ortho.*, 375:30-42 (Jun. 2000).

Baixaull, et al., "A Reinforced Rigid Fixation Device for Unstable Intertrochanteric Fractures," *Clin. Ortho*, 1(361):205-215 (Apr. 1999).

Elder, et al., "Biomechanical Evaluation of Calcium Phosphate Cement-Augmented Fixation of Unstable Intertrochanteric Fractures," *JOT*, 14(6):386-393 (Aug. 2000).

Roberts, et al., Second Generation Intramedullary Nailing of Subtrochanteric Femur Fractures: A Biomechanical Study of Fracture Site Motion, *JOT*, 16(4):231-238 (Apr. 2002).

Robinson, et al., Implant-Related Fractures of the Femur Following Hip Fracture Surgery, *JBJS*, 84(7):1116 (2002).

International Search Report in related International Application No. PCT/US2007/006986.

* cited by examiner

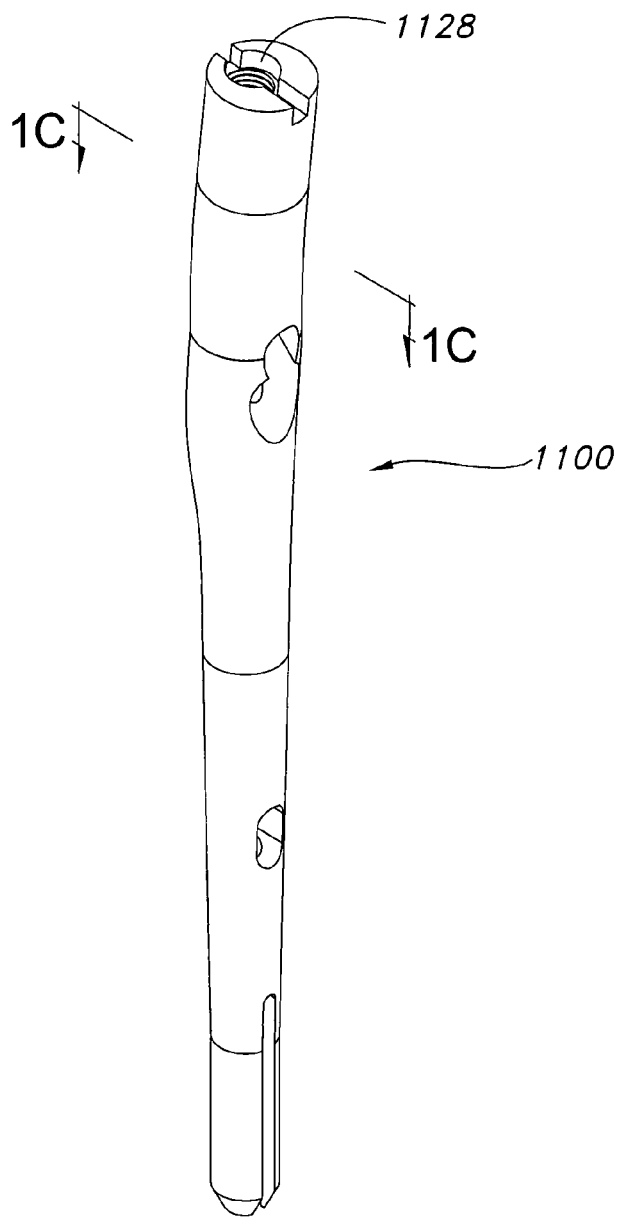
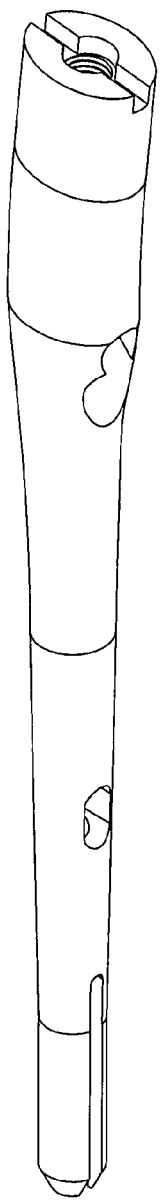
FIG. 1B  FIG. 1D
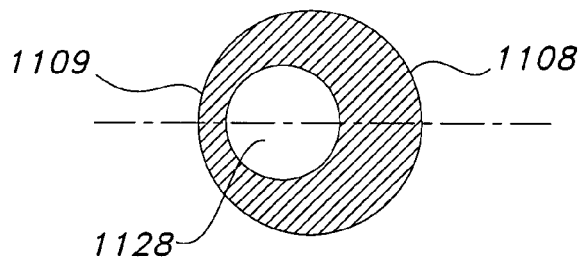
FIG. 1C

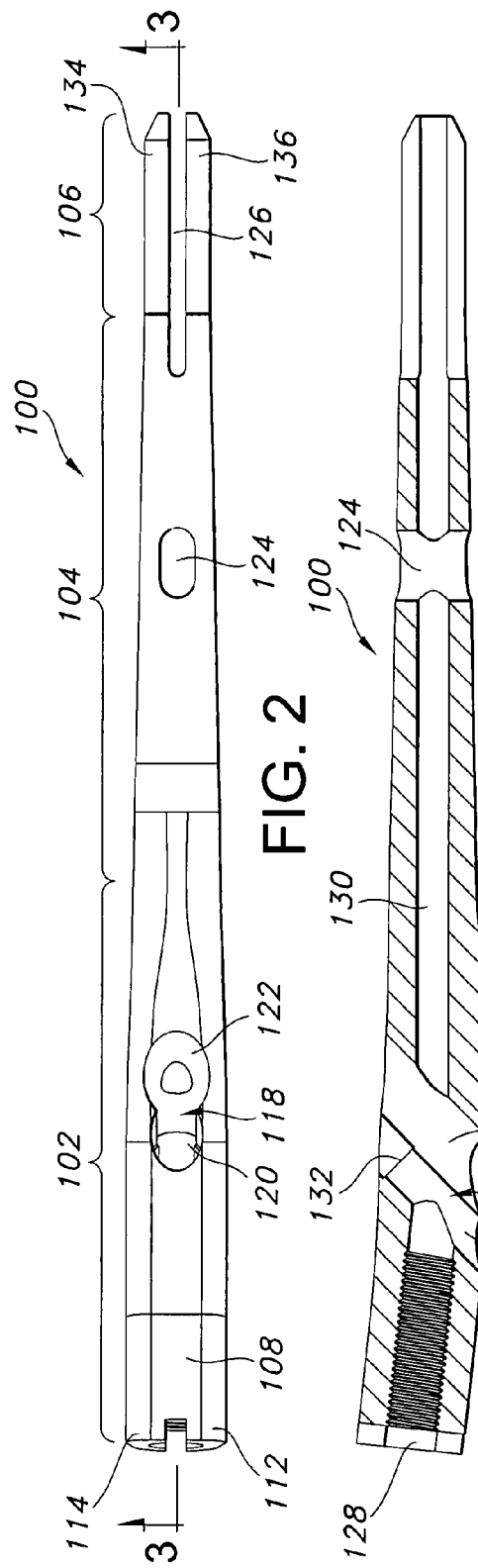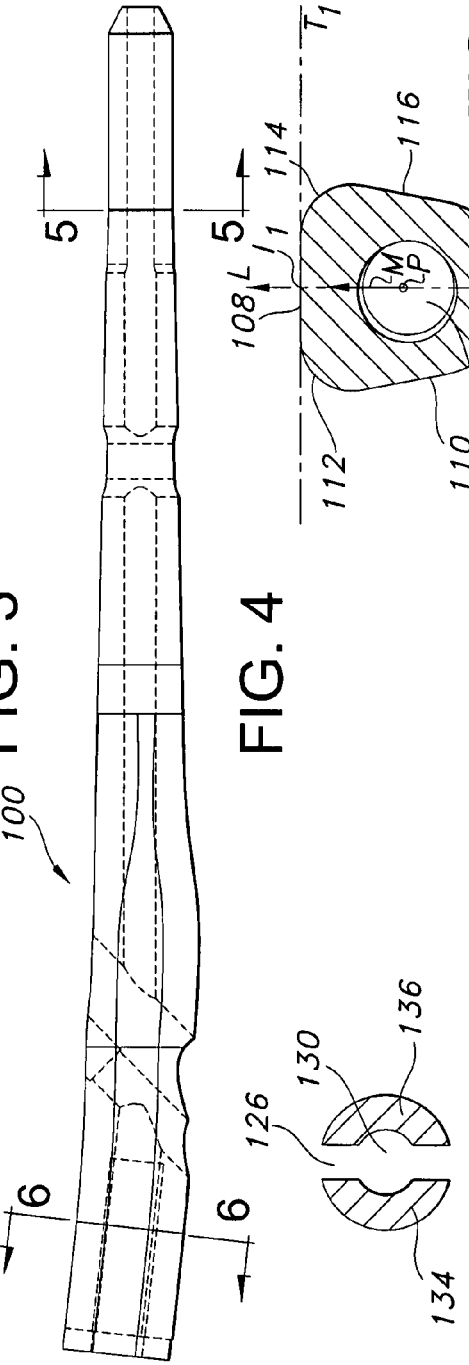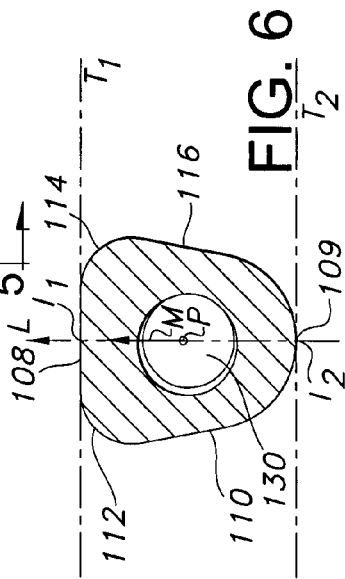

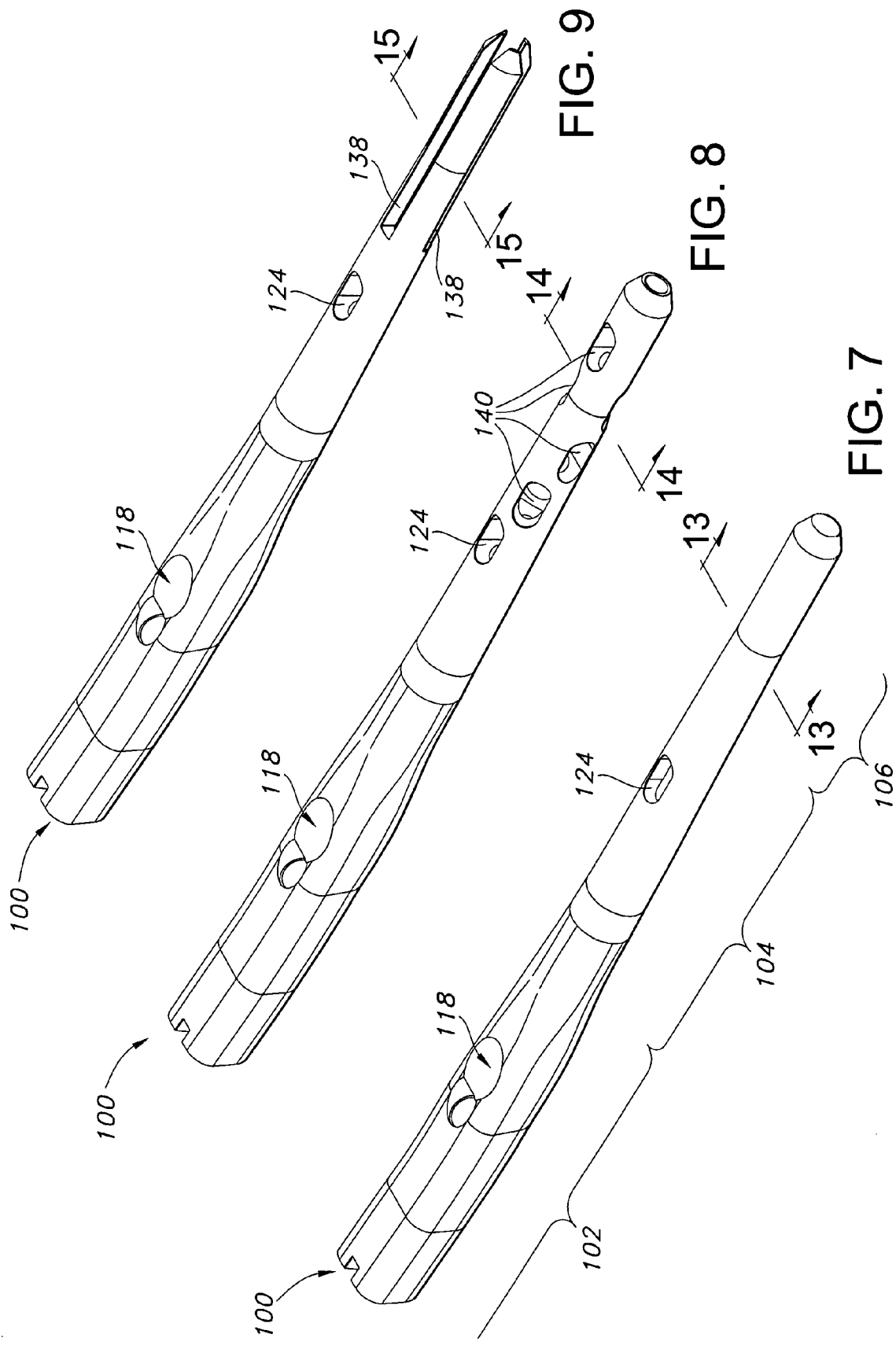

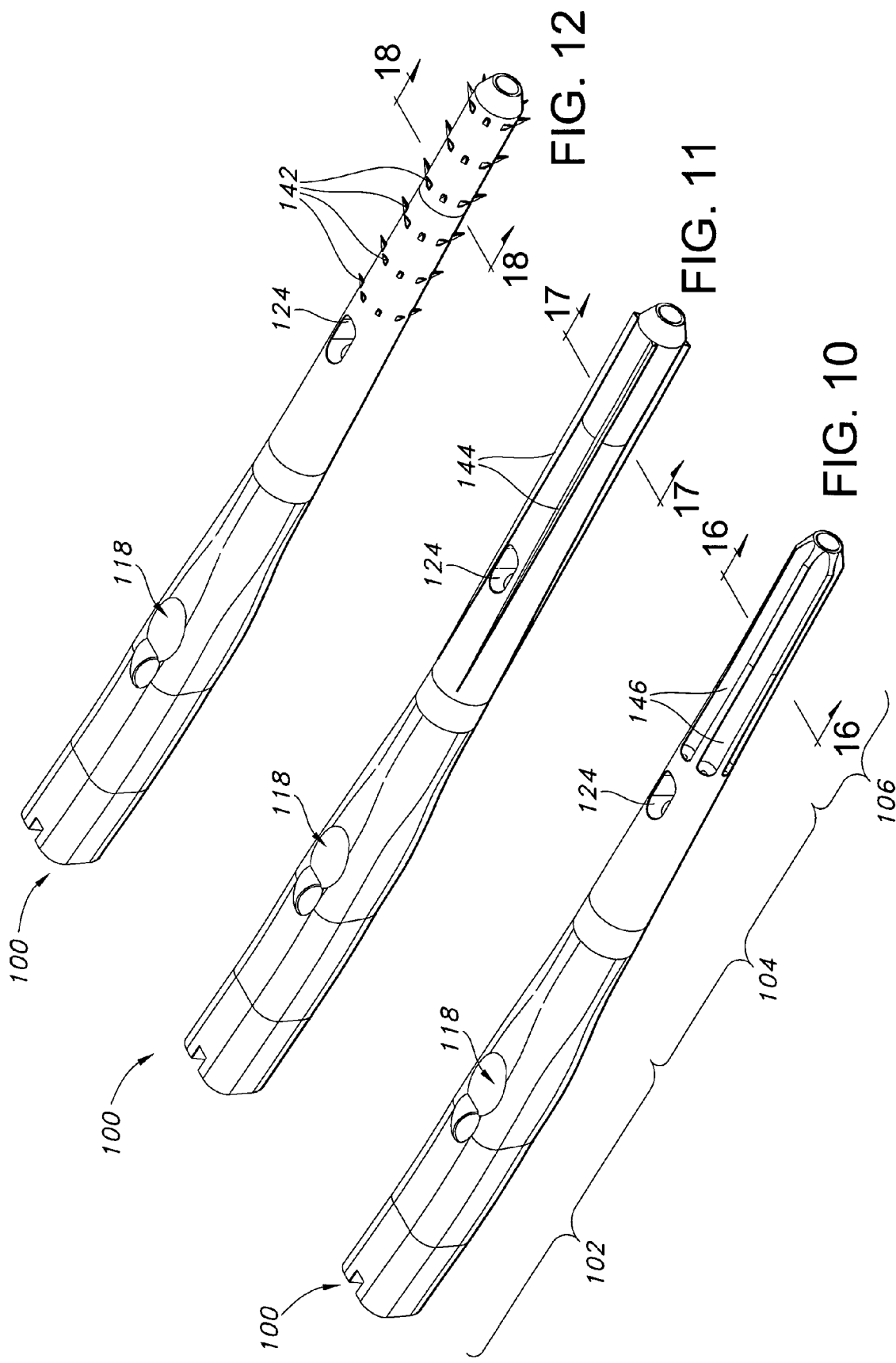

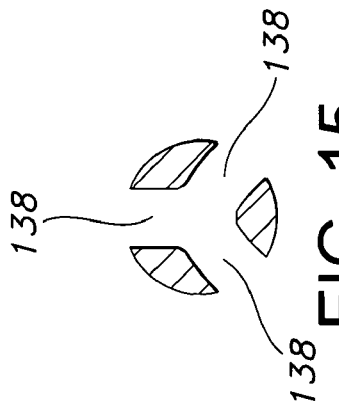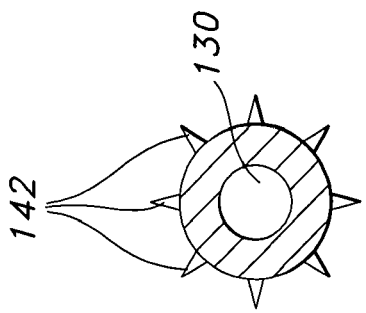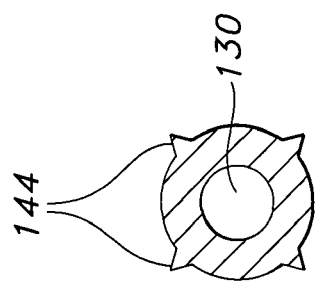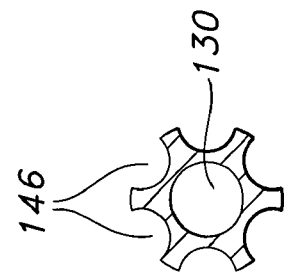

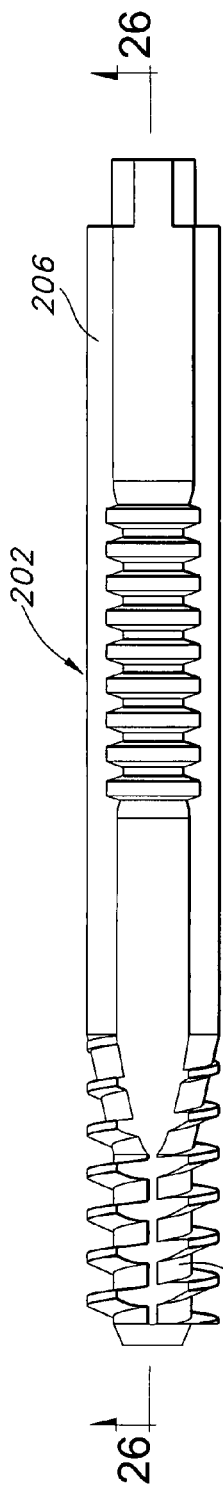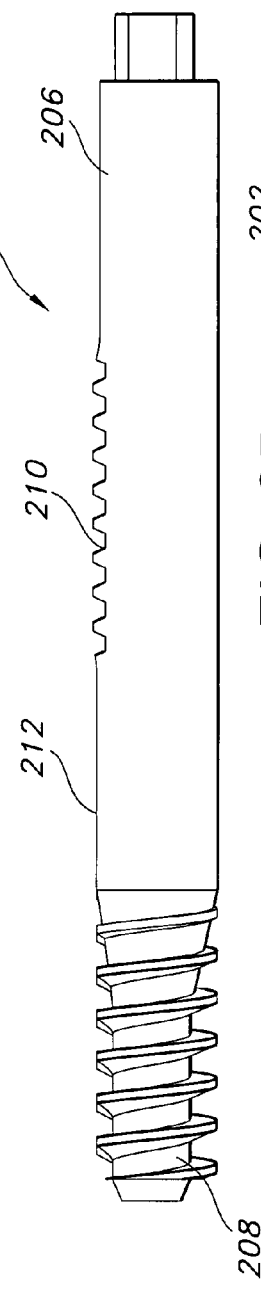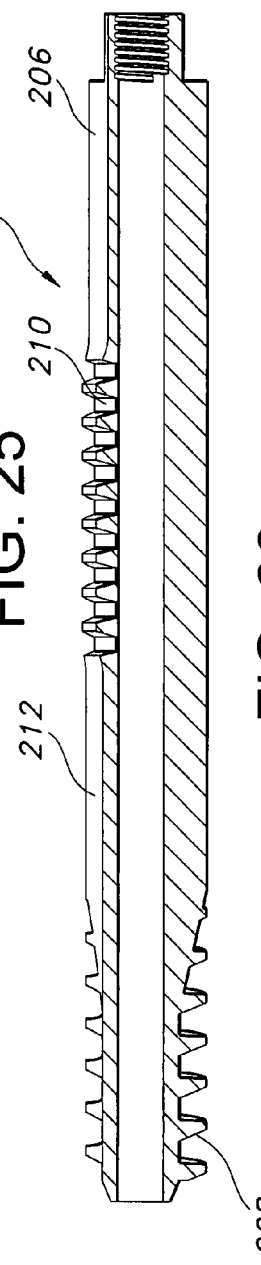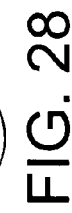
FIG. 24
FIG. 25
FIG. 26
FIG. 27
FIG. 28

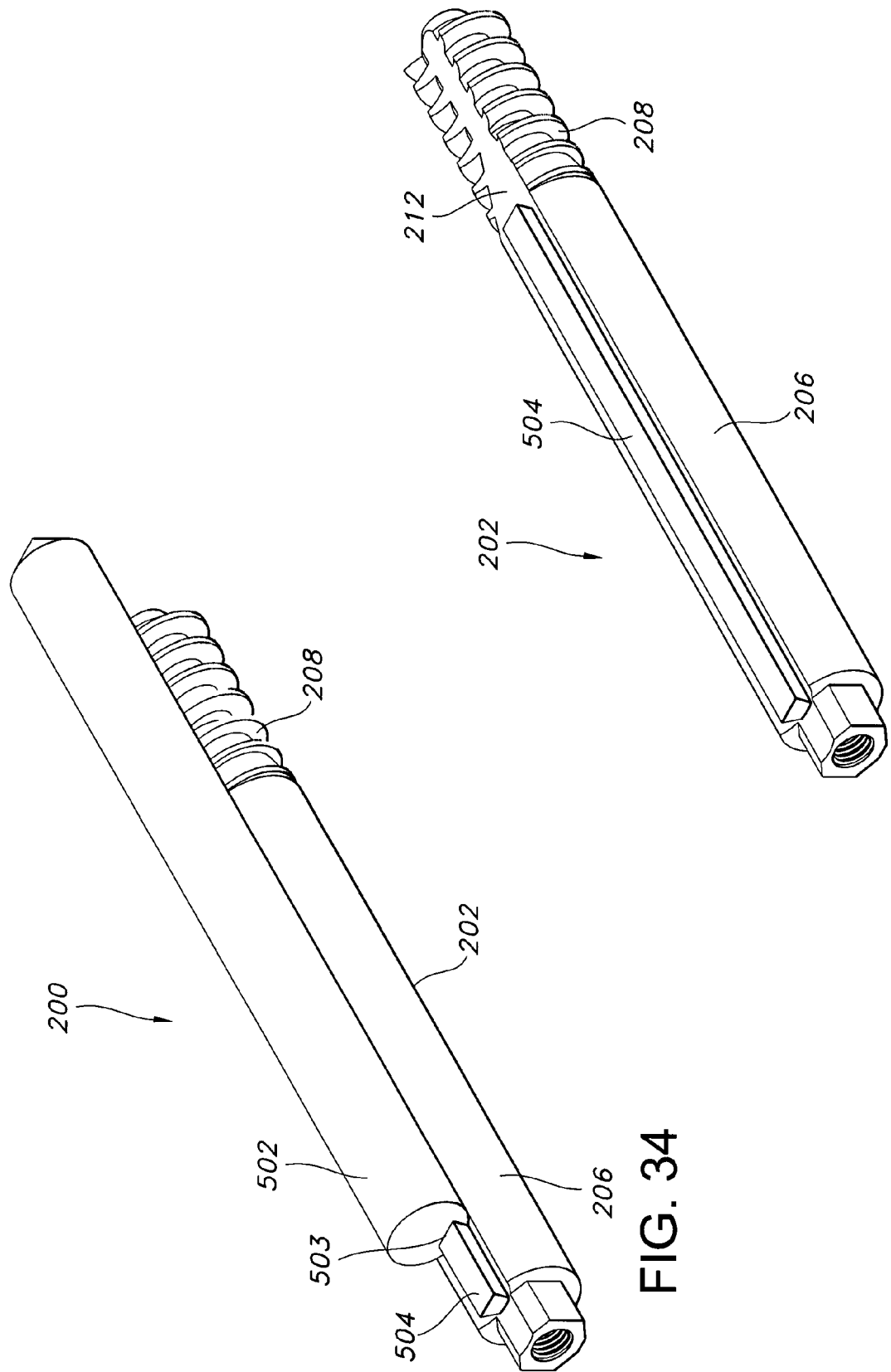

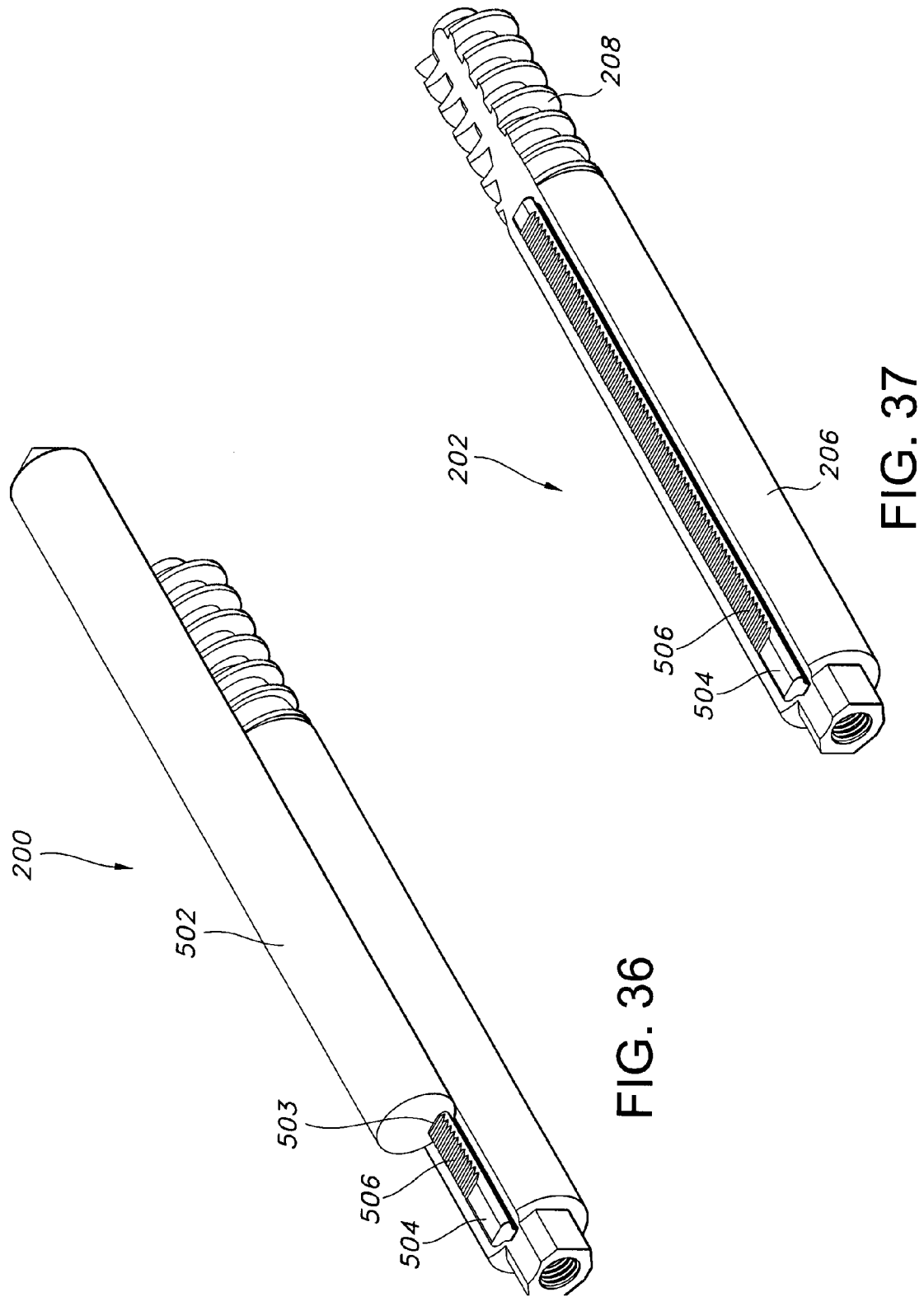

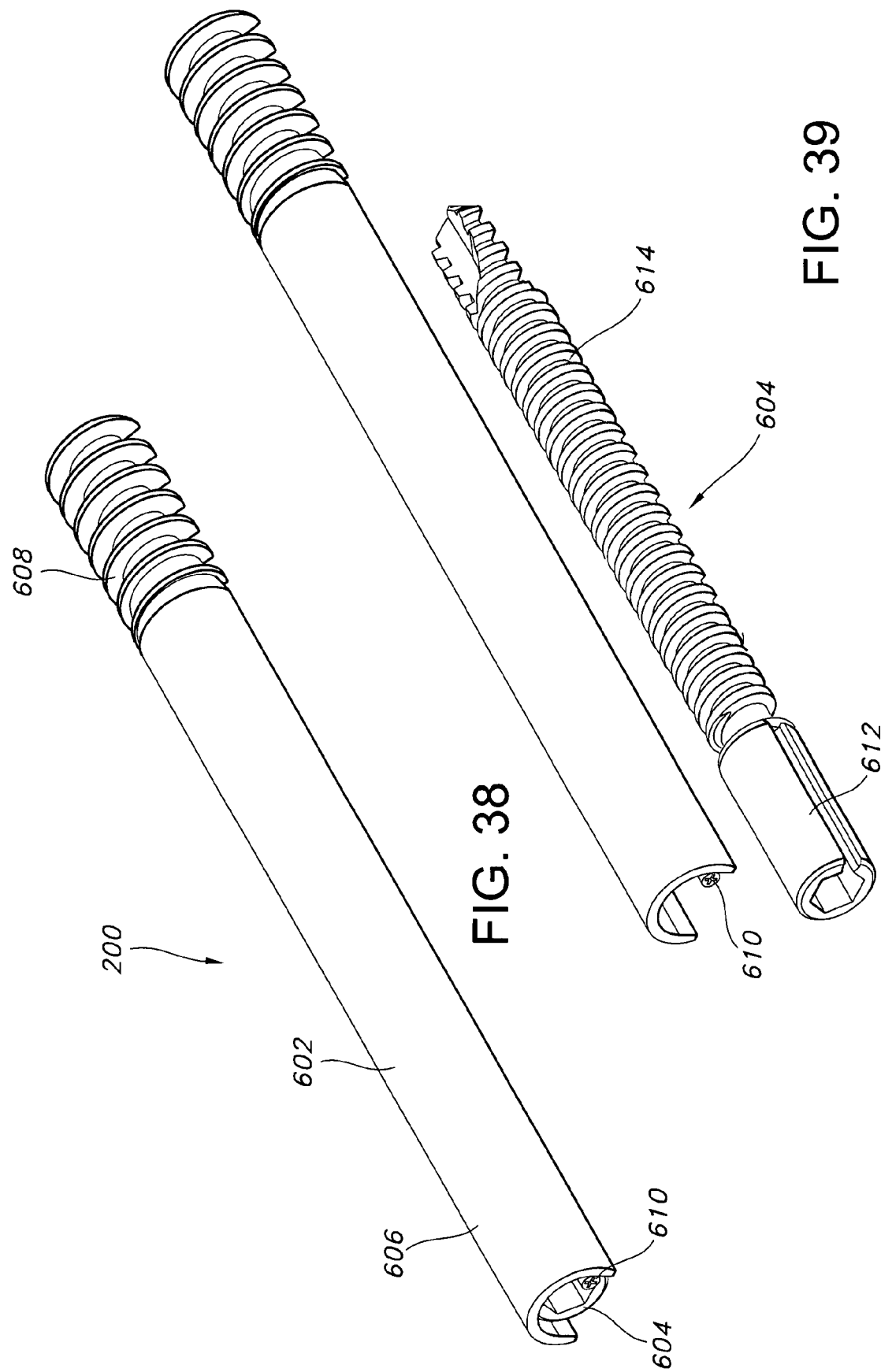

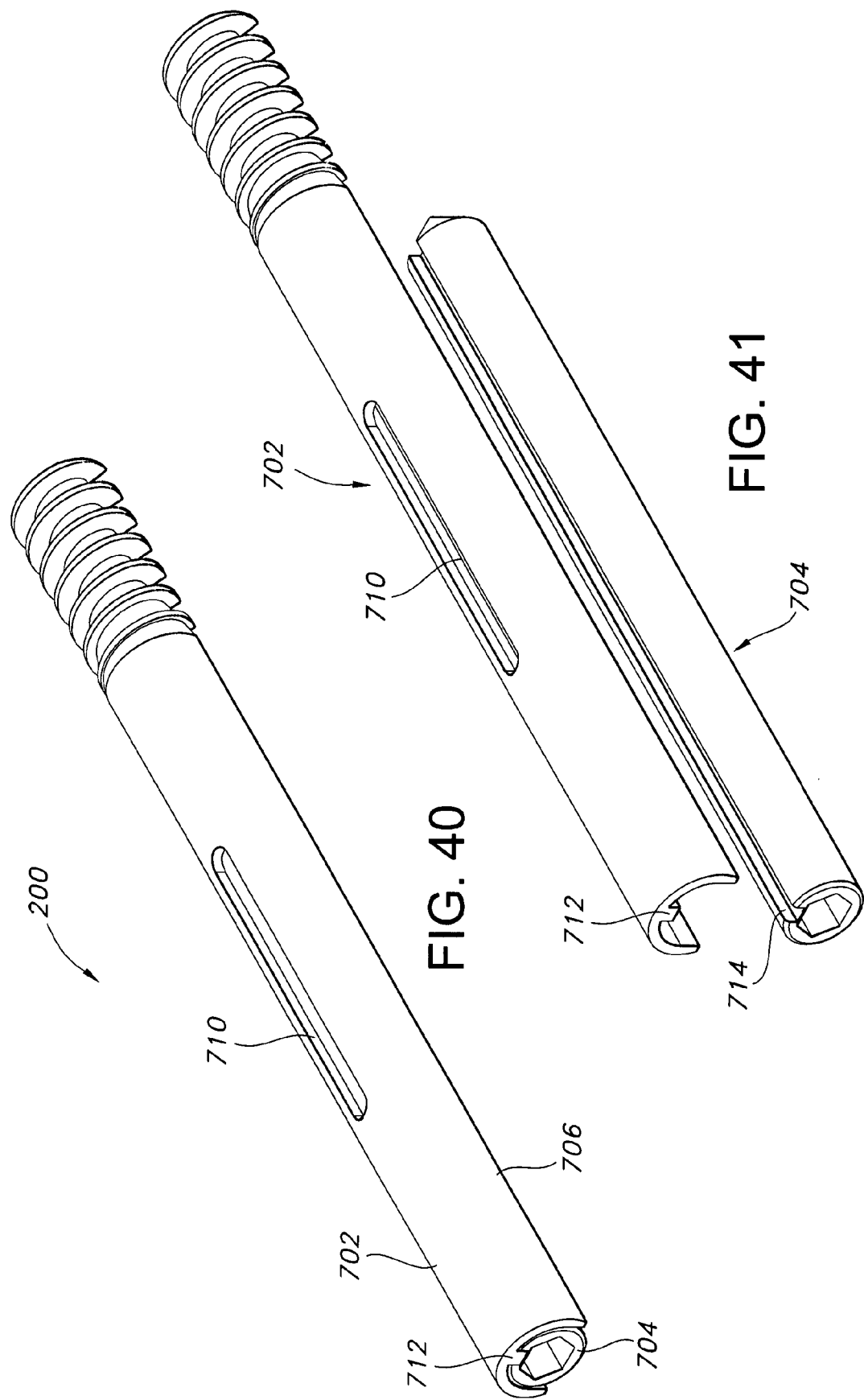

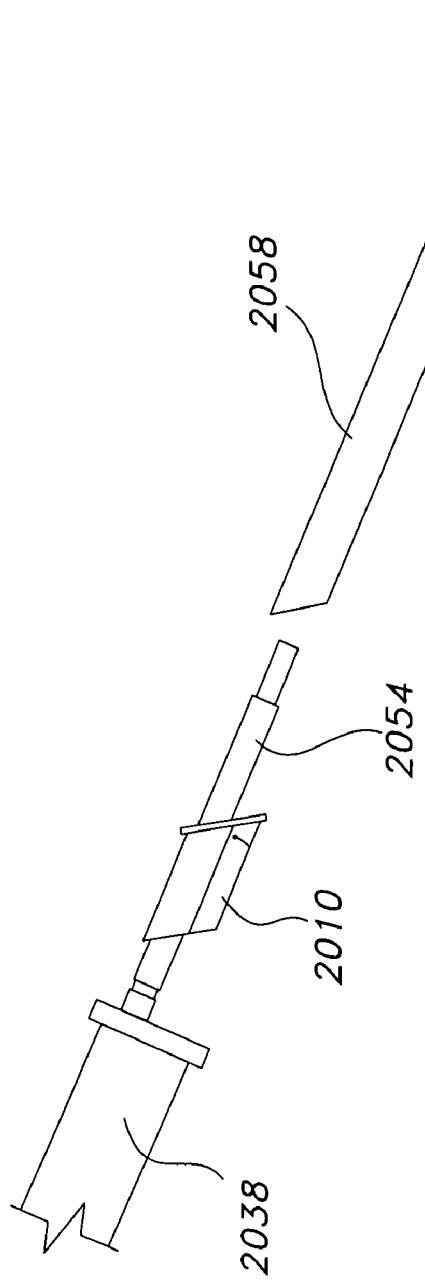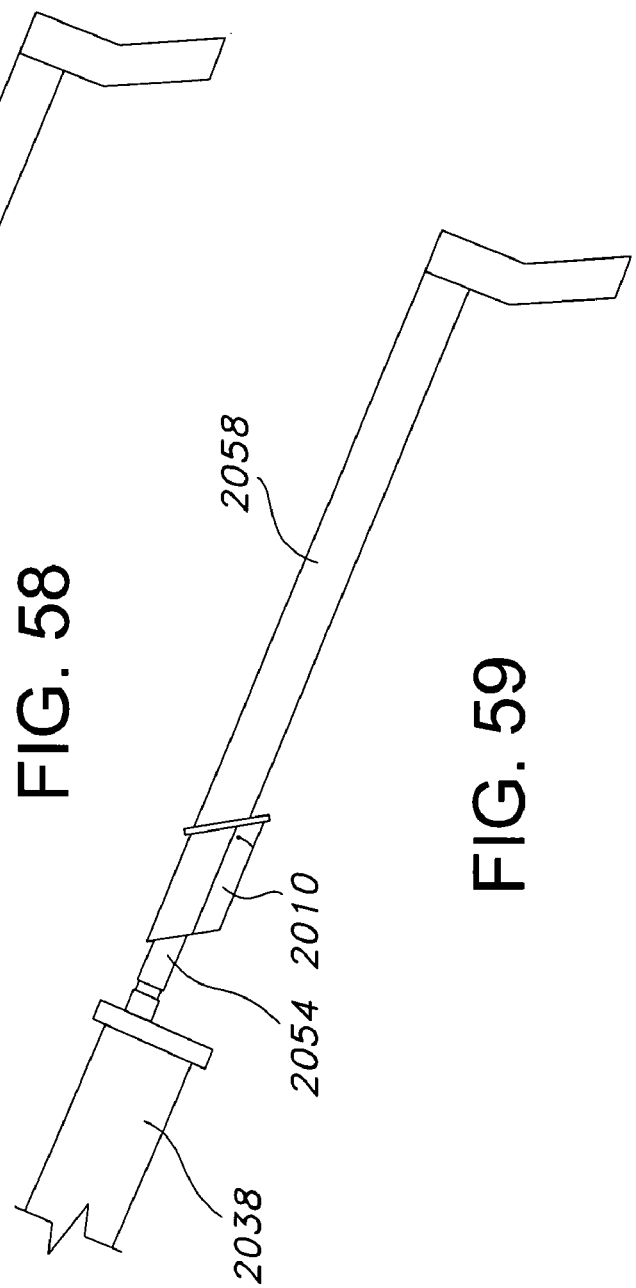

ORTHOPAEDIC PLATE AND SCREW ASSEMBLY

RELATED APPLICATIONS

This application is a continuation-in-part of U.S. application Ser. No. 10/937,075, filed Sep. 8, 2004 now U.S. Pat. No. 7,534,244 for an "Orthopaedic Plate and Screw Assembly," which was a continuation of U.S. application Ser. No. 10/658,351, filed Sep. 8, 2003 now abandoned for an "Orthopaedic Implant and Screw Assembly," the entire contents of both of which are incorporated by this reference. This application also claims the benefit of U.S. provisional application Ser. No. 60/783,931, filed Mar. 20, 2006 for an "Orthopaedic Plate and Screw Assembly," the entire contents of which are incorporated by this reference.

RELATED FIELDS

Embodiments of the present invention generally relate to systems for coupling bone portions across a fracture and, more specifically, to intramedullary nail or plate and screw assemblies or other stabilizing structures and fastening assemblies used to treat fractures of long bones, such as the femur, humerus, tibia, and various periarticular fractures of these and other bones.

BACKGROUND

There are a variety of devices used to treat fractures of the femur, humerus, tibia, and other long bones. For example, fractures of the femoral neck, head, and intertrochanteric region have been successfully treated with a variety of compression screw assemblies, which include generally a compression plate having a barrel member, a lag screw and a compressing screw. Examples include the AMBI® and CLASSIC® compression hip screw systems offered by Smith & Nephew, Inc. In such systems, the compression plate is secured to the exterior of the femur, and the barrel member is inserted in a predrilled hole in the direction of the femoral head. The lag screw has a threaded end, or another mechanism for engaging bone, and a smooth portion. The lag screw is inserted through the barrel member so that it extends across the break and into the femoral head. The threaded portion engages the femoral head. The compression screw connects the lag screw to the plate. By adjusting the tension of the compression screw, the compression (reduction) of the fracture can be varied. The smooth portion of the lag screw is free to slide through the barrel member to permit the adjustment of the compression screw. Some assemblies of the prior art use multiple screws to prevent rotation of the lag screw relative to the compression plate and barrel member and also to prevent rotation of the femoral head on the lag screw.

Intramedullary nails in combination with lag screws or other screw assemblies have been successfully used to treat fractures of the femur, humerus, tibia, and other long bones as well. A significant application of such devices has been the treatment of femoral fractures. One such nailing system is the IMHS® system offered by Smith & Nephew, Inc., and covered at least in part by U.S. Pat. No. 5,032,125 and various related international patents. Other seminal patents in the field include U.S. Pat. Nos. 4,827,917, 5,167,663, 5,312,406, and 5,562,666, which are all assigned to Smith & Nephew, Inc. A typical prior art intramedullary nail may have one or more transverse apertures through its distal end to allow distal bone screws or pins to be screwed or otherwise inserted through the femur at the distal end of the intramedullary nail. This is called "locking" and secures the distal end of the intramedullary nail to the femur. In addition, a typical intramedullary nail may have one or more apertures through its proximal end to allow a lag screw assembly to be screwed or otherwise inserted through the proximal end of the intramedullary nail and into the femur. The lag screw is positioned across the break in the femur and an end portion of the lag screw engages the femoral head. An intramedullary nail can also be used to treat shaft fractures of the femur or other long bones.

As with compression hip screw systems, intramedullary nail systems are sometimes designed to allow compression screws and/or lag screws to slide through the nail and thus permit contact between or among the bone fragments. Contact resulting from sliding compression facilitates faster healing in some circumstances. In some systems, two separate screws (or one screw and a separate pin) are used in order, among other things, to prevent rotation of the femoral head relative to the remainder of the femur, to prevent penetration of a single screw beyond the femoral head, and to prevent a single screw from tearing through the femoral neck and head. When an additional screw or pin is used, however, unequal forces applied to the separated screws or pins can cause the separate screws or pins to be pressed against the sides of the holes through which the separate screws or pins are intended to slide. This may result in binding, which reduces the sliding of the screws or pins through the nail. Conversely, a problem can result from excessive compression of the femoral head toward or into the fracture site. In extreme cases, excessive sliding compression may cause the femoral head to be compressed all the way into the trochanteric region of the femur.

Furthermore, overly rigid nails sometimes generate periprosthetic fractures in regions away from a fracture site. Therefore, it is important that intramedullary nails be adequately flexible in comparison to the bones in which they are implanted.

The harder, generally outer portion of a typical bone is referred to as cortical bone. Cortical bone is usually a structurally sound load-bearing material for support of an implant. A cross-section of a long bone that shows the typical anatomical shape of cortical bone generally reveals a non-circular ring of cortical bone which surrounds a medullary canal. Accordingly, the medullary canal generally features a non-circular cross section. Intramedullary nails of the prior art, however, are usually round or square in cross-section, and therefore not anatomically consistent with the cortical bone or the medullary canal. Some have addressed this problem by reaming the medullary canal of the bone with a round reamer in order to cause the nail to fit the cortical bone. This approach, however, can remove significant portions of healthy cortical bone.

The problem of providing an effective load bearing physical relationship between an implant and cortical bone in the proximal femur has been addressed in the art of hip replacement devices. Various hip stems have been developed which feature generally non-circular cross sections along their length, in order better to fit the anatomically shaped cortical bone of the proximal femur and thus more evenly and effectively distribute the load between the stem and the bone. However, none of these hip stems have been incorporated into a nail, bone plate, or other implant or stabilizing structure, nor have they been configured to accept a screw or screws useful in repairing substantially all of the portions of the treated bone. Instead, hip stems as a general matter have been considered as a device for replacing portions of a long bone, and designed and used for that purpose. For example, the typical application of a hip stem includes completely removing a femoral head and neck, implanting a hip stem, and using the hip stem to support an artificial femoral head.

In summary, and without limitation, the foregoing shows some of the shortcomings of the state of the art in this field. Among other things, what is needed is an orthopaedic system that includes a superior sliding screw or other mechanism for applying compression across a fracture. Some embodiments would also provide a sliding screw or other mechanism that obtains adequate bone purchase while reducing the incidence of cut-out, rotational instability, and excessive sliding. An anatomically appropriately shaped implant or other stabilizing structure for achieving improved cortical bone contact would also be advantageous. Where the stabilizing structure is an intramedullary nail implant, the nail would provide for reduced reaming and removal of healthy bone. An improved stabilizing structure may also have a cross-section that provides a greater area of material on the side of the device that is placed under a greater tensile load when it is subjected to a typical bending load. Additionally, an improved orthopaedic system could include a sliding screw in combination with intramedullary nails of various designs, or in combination with plates or other stabilizing structures. Combinations of any of these with each other, and/or with other devices or combinations of them also present opportunities for advancement beyond the state of the art according to certain aspects and embodiments of the present invention.

SUMMARY

Methods, devices and systems according to certain aspects of this invention allow treatment of bone fractures and other types of maladies using one or both of a stabilizing structure for association with a first bone fragment and a fastening assembly for association with a second bone fragment. The stabilizing structure may be a plate or other device for at least partial application to the outer surface of bone, or an implant for at least partial implantation within bone. Such stabilizing structures may include a proximal section having a transverse aperture.

In some embodiments, one or more cross sections of the proximal section may feature shapes that impart additional strength and resistance to tension. Such shapes can be provided, for instance, by one or both (i) adding additional mass in lateral portions of the cross section, and (2) strategically adding and reducing mass in the cross section to take advantage of flange effects similar to the way flanges add structural benefits to I-beams and channels. One way to characterize such cross-sections, which can but need not be asymmetrical with respect to at least one axis, is that they generally feature a moment of inertia extending in a lateral direction from a point that is the midpoint of a line from a lateral tangent to a medial tangent of the cross section. In some structures, that line is coplanar with the axis of the transverse aperture and coplanar with the cross section and thus defined by the intersection of those planes. The endpoints of that line can be defined as the intersection of the line with tangents to the medial aspect and the lateral aspect of the cross section, respectively. In some embodiments, such stabilizing structures may also include a transition section to provide a coupling between proximal and distal sections of the stabilizing structure. In other embodiments, it is not necessary that the stabilizing structure include these geometries and/or properties.

Fastening assemblies of methods, devices and systems according to certain embodiments of the invention may at least partially extend through the transverse aperture of the stabilizing structure and may include an engaging member and a compression member. The engaging member may be a lag screw or other similar device used to gain purchase in or otherwise engage a second bone fragment. The engaging member may be able to slide with respect to the transverse aperture of the stabilizing structure. The engaging and compression members may be configured such that the compression member at least indirectly interacts with a portion of the stabilizing structure as well as a portion of the engaging member to enable controlled movement between the first and second bone fragments. In some embodiments, the compression member at least partially directly contacts the second bone fragment.

In some embodiments, methods, devices, and systems of the present invention include an insert received in the stabilizing structure's transverse aperture that includes another transverse aperture. In such embodiments, the fastening assembly may at least partially extend through the second transverse aperture.

According to an aspect of the present invention, there may be provided an apparatus for treating bone maladies, including a stabilizing structure associated with a first bone portion, the stabilizing structure including a first transverse aperture; a fastening assembly at least partially extending through the first transverse aperture, the fastening assembly including an engaging member and a compression member: the engaging member engaging a second bone portion; the compression member contacting and interacting with the engaging member; the compression member contacting the second bone portion; and the compression member at least indirectly interacting with the stabilizing structure; and an insert at least partially extending through the first transverse aperture and including a second transverse aperture; the fastening assembly at least partially extending through the second transverse aperture.

According to some embodiments of the present invention, the compression member facilitates a sliding movement of the engaging member with respect to the first transverse aperture; and the compression member facilitates a controlled movement between the first and second bone portions.

According to some embodiments of the present invention, the compression member at least indirectly interacts with the insert to facilitate controlled movement between the first and second bone portions.

According to some embodiments of the present invention, the compression member includes a shoulder that abuts against a portion of the insert.

According to some embodiments of the present invention, the controlled movement between the first and second bone portions includes substantial preclusion of rotation of the first and second bone portions with respect to one another.

According to some embodiments of the present invention, the controlled movement between the first and second bone portions includes compressing the first and second bone portions with respect to one another.

According to some embodiments of the present invention, adjusting the compression member tensions the engaging member to compress the first and second bone portions with respect to one another.

According to some embodiments of the present invention, the compression member is at least partially nested within a portion of the engaging member.

According to some embodiments of the present invention, the compression member includes a first threaded portion and the engaging member includes a second threaded portion; wherein the first and second threaded portions cooperate with one another such that adjusting the compression member tensions the engaging member to compress the first and second bone portions with respect to one another.

According to some embodiments of the present invention, the insert snaps into the first transverse aperture.

According to some embodiments of the present invention, an arm interacts with an indention to facilitate the insert snapping into the first transverse aperture.

According to some embodiments of the present invention, a ridge member interacts with an indention to facilitate the insert snapping into the first transverse aperture.

According to another aspect of the present invention, there may be provided an apparatus for treating bone maladies, including stabilizing structure associated with a first bone portion, the stabilizing structure including a transverse aperture; a fastening assembly at least partially extending through the first transverse aperture, the fastening assembly including an engaging member and a compression member, wherein the engaging member engages a second bone portion, wherein the compression member contacts and interacts with the engaging member, wherein the compression member contacts the second bone portion, wherein the compression member facilitates a sliding movement of the engaging member with respect to the first transverse aperture, wherein the compression member at least indirectly interacts with the stabilizing structure to facilitate controlled movement between the first and second bone portions, and wherein the controlled movement comprises substantial preclusion of rotation of the first and second bone portions with respect to one another as well as compressing the first and second bone portions with respect to one another; and an insert at least partially extending through the first transverse aperture and including a second transverse aperture; wherein the fastening assembly at least partially extends through the second transverse aperture.

According to some embodiments of the present invention, the compression member at least indirectly interacts with the insert to facilitate controlled movement between the first and second bone portions.

According to some embodiments of the present invention, the compression member includes a shoulder that abuts against a portion of the insert.

According to some embodiments of the present invention, adjusting the compression member tensions the engaging member to compress the first and second bone portions with respect to one another.

According to some embodiments of the present invention, the compression member is at least partially nested within a portion of the engaging member.

According to some embodiments of the present invention, the compression member includes a first threaded portion and the engaging member includes a second threaded portion, wherein the first and second threaded portions cooperate with one another such that adjusting the compression member tensions the engaging member to compress the first and second bone portions with respect to one another.

According to some embodiments of the present invention, the stabilizing structure is a compression plate.

According to some embodiments of the present invention, the stabilizing structure is a periarticular plate.

According to some embodiments of the present invention, the insert snaps into the first transverse aperture.

According to some embodiments of the present invention, the insert is integral with the stabilizing structure.

According to another aspect of the present invention, there may be provided a method for treating bone maladies including the steps of: associating a stabilizing structure with a first bone portion, the stabilizing structure including a first transverse aperture; engaging an engaging member with a second bone portion; at least partially inserting an insert through the first transverse aperture; the insert including a second transverse aperture; and passing a compression member at least partially through the second transverse aperture; the compression member at least indirectly interacting with the stabilizing structure; the compression member contacting the second bone portion; the compression member contacting and interacting with the engaging member; and the engaging member at least partially extending through the second transverse aperture.

According to some embodiments of the present invention, a method for treating bone maladies also includes using the compression member to facilitate a sliding movement of the engaging member with respect to the stabilizing structure, the compression member at least indirectly interacting with the stabilizing structure to facilitate controlled movement between the first and second bone portions.

According to some embodiments of the present invention, a method for treating bone maladies also includes associating a guide with the stabilizing structure; and using the guide to guide the movement of at least one bone preparation instrument.

According to some embodiments of the present invention, the guide is used to guide the movement of a plurality of bone preparation instruments.

According to some embodiments of the present invention, the guide is used to guide the movement of the at least one bone preparation instrument after the stabilizing structure has been associated with the first bone portion.

According to some embodiments of the present invention, the engaging member is engaged with the second bone portion after the stabilizing structure is associated with the first bone portion and after the guide is used to guide the movement of the at least one bone preparation instrument.

According to some embodiments of the present invention, the insert is at least partially inserted through the first transverse aperture after the stabilizing structure is associated with the first bone portion.

According to some embodiments of the present invention, using the compression member to facilitate a sliding movement of the engaging member facilitates compressing the second bone portion with respect to the first bone portion.

'Embodiment' as used herein can be considered to mean an aspect or object of the invention, and vice versa.

BRIEF DESCRIPTION OF DRAWINGS

FIG. 1B is a perspective view of an intramedullary nail according to another embodiment of the present invention.

FIG. 1C is a cross-sectional view of a portion of the nail of FIG. 1B.

FIG. 1D is a perspective view of an intramedullary nail according to another embodiment of the present invention.

FIG. 2 is an elevation view of the intramedullary nail of FIG. 1.

FIG. 3 is a cross-section view of the intramedullary nail of FIG. 2 taken through the line 3-3.

FIG. 4 is a side view of the intramedullary nail of FIG. 2.

FIG. 5 is a cross-section view of the intramedullary nail of FIG. 4 taken through the line 5-5.

FIG. 6 is a cross-section of the intramedullary nail of FIG. 4 taken through the line 6-6.

FIG. 7 is a perspective view of an intramedullary nail according to an alternative embodiment of the invention.

FIG. 8 is a perspective view of an intramedullary nail according to an alternative embodiment of the invention.

FIG. 9 is a perspective view of an intramedullary nail according to an alternative embodiment of the invention.

FIG. 10 is a perspective view of an intramedullary nail according to an alternative embodiment of the invention.

FIG. 11 is a perspective view of an intramedullary nail according to an alternative embodiment of the invention.

FIG. 12 is a perspective view of an intramedullary nail according to an alternative embodiment of the invention.

FIG. 13 is a cross-section view of the intramedullary nail of FIG. 7 taken through line 13-13.

FIG. 14 is a cross-section view of the intramedullary nail of FIG. 8 taken through line 14-14.

FIG. 15 is a cross-section view of the intramedullary nail of FIG. 9 taken through line 15-15.

FIG. 16 is a cross-section view of the intramedullary nail of FIG. 10 taken through line 16-16.

FIG. 17 is a cross-section view of the intramedullary nail of FIG. 11 taken through line 17-17.

FIG. 18 is a cross-section view of the intramedullary nail of FIG. 12 taken through line 18-18.

FIG. 24 is an elevation view of the engaging member of the fastener assembly of FIG. 23.

FIG. 25 is a side view of the engaging member of FIG. 24.

FIG. 26 is a cross-section view of the engaging member of FIG. 24 taken through line 26-26.

FIG. 27 is an end view of one end of the engaging member of FIG. 24

FIG. 28 is an end view of the other end of the engaging member of FIG. 24.

FIG. 34 is a perspective view of a fastener assembly according to another embodiment of the invention.

FIG. 35 is a perspective view of the lag screw of the fastener assembly of FIG. 34.

FIG. 36 is a perspective view of a fastener assembly according to another embodiment of the invention.

FIG. 37 is a perspective view of the lag screw of the fastener assembly of FIG. 36.

FIG. 38 is a perspective view of a fastener assembly according to another embodiment of the invention.

FIG. 39 is an exploded view of the fastener assembly of FIG. 38.

FIG. 40 is a perspective view of a fastener assembly according to another embodiment of the invention.

FIG. 41 is an exploded view of the fastener assembly of FIG. 40.

FIGS. 48-60 show various instruments and illustrate various methodologies that may, in some embodiments, be used to install apparatuses according to some embodiments of the present invention.

DETAILED DESCRIPTION OF DRAWINGS

Figure 1:
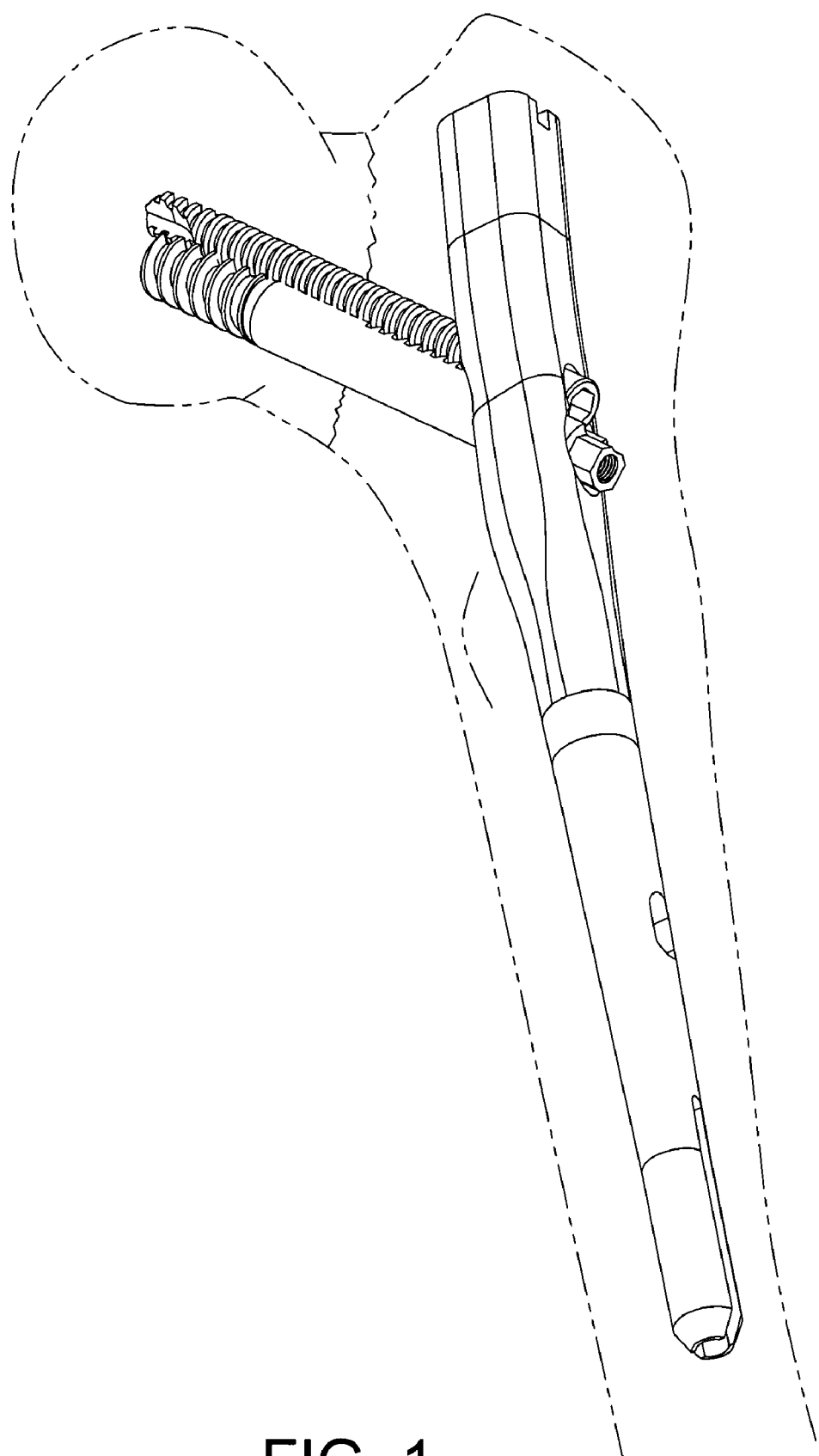
FIG. 1 is a perspective view of an intramedullary nail according to one embodiment of the present invention shown installed in a femur.

Methods, devices and systems according to embodiments of this invention may seek to provide improved treatment of femur fractures and other types of bone maladies. FIGS. 1-6 illustrate various views of one embodiment of an intramedullary nail 100 of the present invention. The intramedullary nail 100 has a longitudinal bore 130 throughout to aid in insertion in the bone. The intramedullary nail 100 has a proximal section 102, a transition section 104 and a distal section 106.

In some embodiments, the proximal section 102 of the particular structure shown in FIGS. 1-6 may feature an anatomically inspired shape that corresponds more accurately to typical cortical bone. One version of such shape is shown in the cross-sectional view of the proximal section 102 in FIG. 6. The particular cross-section of the proximal section 102 shown in FIG. 6 is generally non-circular along at least some portions of its length, and has a lateral side or aspect 108 that is larger than a medial side or aspect 109. The lateral side 108 and medial side 109 are joined by a first side 110 and a second side 116. At the intersection of the first side 110 with the lateral side 108 is a first radiused corner 112 and at the intersection of the second side 116 with the lateral side 108 is a second radiused corner 114. The first side 110, second side 116 and lateral side 108 are of approximately equal length. The first side 110 and second side 116 are oriented at acute angles relative to the lateral side 108, so that the medial side 109 is smaller than the lateral side 108. By having the lateral side 108 larger than the medial side 109 the rotational stability of the intramedullary nail 100 is increased, and resistance to bending and twisting can also be enhanced.

The medial side 109 shown in FIG. 6 can be radiused. As can be seen in FIG. 4, the radiused medial side 109 protrudes out from the transition section 104 and continues to the proximal end of the intramedullary nail 100. The protrusion of the medial side 109 corresponds to the calcar region of the femur and improves the evenness of load distribution between the bone and intramedullary nail 100.

Furthermore, the general cross-section geometry of the proximal section reduces peak stresses in the proximal section. More specifically, the typical failure mode of an intramedullary nail and screw assembly combination is failure of the nail in tension on its lateral side. The tension is created by bending moment induced by body weight load that is applied to the screw assembly. Therefore, it would be beneficial in reducing stress in the proximal section of a nail to include more material on the side of the nail that is in tension, the lateral side, to shape the cross section more effectively to enhance strength and robustness in the lateral area, or both. The design illustrated in FIG. 6 accomplishes this. The lateral side 108 is wider than the medial side 109, thus imparting, at least partially, a flange-like effect. Stress per unit area induced in the material on the lateral side 108 is less than would be the case if the lateral side was featured a smaller cross-sectional area, such as medial side 109.

A structure according to another embodiment of the invention that benefits from the same principle is shown in FIGS. 1B and 1C, which illustrate an intramedullary nail 1100 with a generally circular cross section whose generally circular aperture 1128 is disposed other than concentric with the periphery of the cross section. In the particular structure shown in these two Figures, the offset aperture 1128 is offset toward the medial side 1109 such that a greater portion of material is available to take load, and reduce stress, on the lateral side 1108. Likewise, any cross-section that provides more material on the lateral side of the section reduces stress per unit area in the nail on that side.

Regardless of the particular manner in which material or mass may be added to some portions of the lateral parts of the cross section of proximal portion 102, material may be added and removed from some portions of the cross section in order to increase the strength and robustness of the lateral parts, or both, the effect can be characterized as imparting a moment of inertia to the cross section oriented at least partially in the direction of the lateral side or aspect 108. In some embodiments, the moment of inertia (shown denoted by the letter M on FIG. 6) can be characterized as extending in a lateral direction, or at least partially toward lateral aspect or side 108 from a point P that is the midpoint of a line L extending from the intersection I1 of that line with a tangent T1 to the lateral aspect 108, to the intersection I2 of that line with a tangent T2 to the medial aspect 109. Stated another way, the effect in at least some cases is to create a cross section that features a moment of inertia extending in an at least partially lateral direction from a center of the cross section. Preferably, that center can be a midpoint between the lateral and medial edges of the cross section. Alternatively, that center can be the center of mass of the cross section. The radius of gyration reflected by the moment of inertia, which is a function of the square of the distance of the incremental mass from the center, reflects additional strength in lateral parts of the proximal portion 102 caused by more mass or more strategically placed mass in the cross section. In some structures, line L is coplanar with the axis of the transverse aperture and coplanar with the cross section and thus defined by the intersection of those planes. As FIG. 1A on the one hand, and 1B and 1C on the other hand, reflect, and bearing in mind that these are only three of a myriad of structures that can impart such lateral additional strength and robustness, the cross section can but need not be asymmetrical with respect to at least one of its axes. Additionally, the longitudinal opening 130 can be located to share its central axis with that of the cross section, or it can be offset in order to help impart the lateral strength or for other purposes.

In the particular devices shown in FIGS. 1, 1A, and 2-6, the first side 110, second side 116 and lateral side 108 are flat. Alternatively, these sides could be radiused or otherwise not flat. In the embodiments shown in FIGS. 1-6, the medial side 109 is radiused, but as one skilled in the art could appreciate, the medial side could be flat.

Figure 1A:
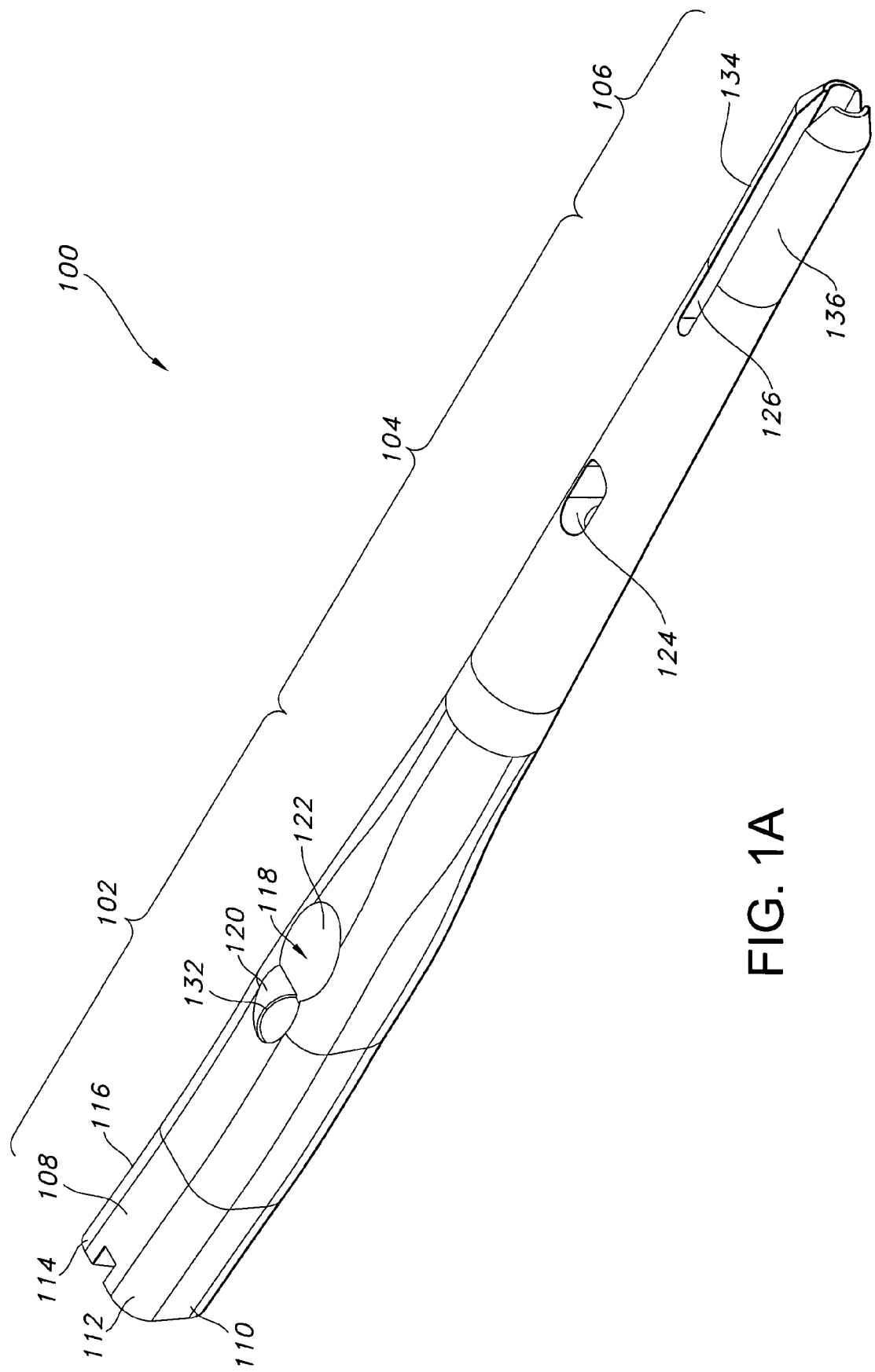
FIG. 1A is a perspective view of an intramedullary nail according to one embodiment of the present invention, shown in greater detail than the intramedullary nail shown in FIG. 1.
Figure 33:
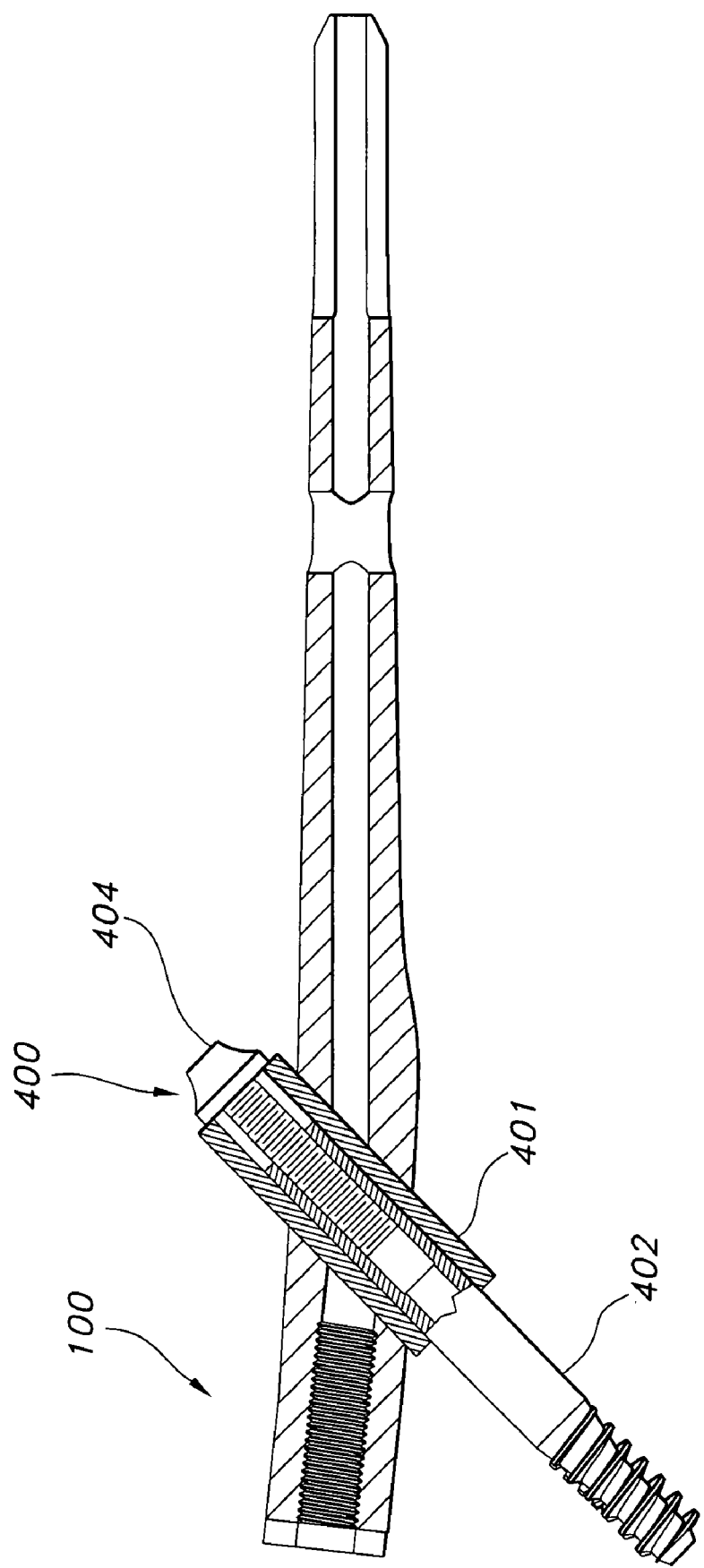
FIG. 33 is a cross-section view of an intramedullary nail and screw assembly according to another embodiment of the present invention.

The proximal section 102 shown in FIG. 1A has a transverse aperture 118 that receives a fastening or screw assembly 200 (various versions of which are shown in FIGS. 20-41) through the intramedullary nail 100. One embodiment of the proximal transverse aperture 118, shown in FIGS. 1-4, is formed from two overlapping circular apertures 120, 122, where the proximal circle aperture 120 is smaller in diameter than the distal circle aperture 122. The proximal circle aperture 120 shown has a shoulder 132 for constraining the insertion depth of the fastening assembly as will be explained in more detail below. Various other apertures allowing insertion of various fastening assemblies could be used as would be known to those skilled in the art. For example, FIG. 33 illustrates the intramedullary nail with a circular aperture. The embodiment of FIG. 33 is described in greater detail below.

The proximal section 102 illustrated in FIG. 3 has a proximal end aperture 128. The proximal end aperture 128 is threaded to allow for the insertion of a set screw that can be used to fix the rotational and sliding position of a fastening assembly. A set screw may also include mechanisms for spanning a compression member 204 and interfering with an engaging member 204 to independently restrict the rotation or sliding of the engaging member 204.

As shown in FIGS. 1-6, the transition section 104 is tapered from the proximal section 102 to the distal section 106. The tapered nature of the transition section 104 creates a press fit in the intramedullary canal that controls subsidence. The tapered transition section 104 assists in preventing the nail 100 from being pressed further down into the intramedullary canal of the femur than intended.

In the intramedullary nail 100 embodiments shown in FIGS. 1-6, the cross-section of the transition section 104 is circular, but the cross-section could vary as known to those skilled in the art. The cross-section could be anatomically derived, similar to the cross-section of the proximal section 102, oval or non-circular. In the embodiment shown in FIGS. 1-6, the transition section 104 contains a distal transverse aperture 124. The distal aperture 124 allows the insertion through the intramedullary nail 100 of a distal locking screw for locking of the intramedullary nail 100.

The distal section 106 of the intramedullary nail 100 is generally cylindrical and is configured to provide a reduced bending stiffness. The embodiments shown in FIGS. 1-5 include a longitudinal slot 126 through the center of the distal section 106 that forms two sides 134, 136. The slot reduces bending stiffness at the distal end of the intramedullary nail 100 and reduces the chances of periprosthetic fractures.

FIG. 1D shows an intramedullary nail 100 according to another embodiment of the invention. This nail features, in its proximal portions, a noncircular cross section that is symmetrical with respect to its lateral—medial axis (in this case, preferably but not necessarily, oval shaped in cross-section), and which features a centered longitudinal bore (in this case, preferably but not necessarily, circular in cross-section). This nail achieves additional stability to the extent it resists twisting in the medullary canal. It also accomplishes the aim of placing more mass toward the lateral edge or aspect of the proximal cross section. Furthermore, it places additional mass toward the medial edge or aspect, and thus provides additional structure that acts as a fulcrum to decrease the mechanical advantage of the fastening assembly which when loaded is the component that imposes tensional stress on the lateral edge or aspect.

FIGS. 7-18 illustrate intramedullary nails 100 according to other embodiments of the invention. FIG. 7 illustrates an intramedullary nail 100 having no longitudinal bore throughout.

FIGS. 8 and 14 illustrate an intramedullary nail 100 having stiffness reduction slots 140 in the transition section 104 and the distal section 106. The stiffness reduction slots 140 reduce the bending stiffness at the distal end of the intramedullary nail 100 and could be used to receive locking screws in some embodiments.

FIGS. 9 and 15 illustrate an intramedullary nail 100 having three longitudinal slots 138 in the distal section 106 and a portion of the transition section 104 forming a cloverleaf pattern. This pattern more readily permits blood flow near the intramedullary nail 100 and also reduces bending stiffness at the distal end of the nail 100.

FIGS. 10 and 16 illustrate an intramedullary nail 100 in which the distal section 106 and a portion of the transition section 104 have a series of longitudinal grooves 146. The longitudinal grooves 146 reduce bending stiffness at the distal end, provide rotational resistance, and enhance blood flow near the intramedullary nail 100.

FIGS. 11 and 17 illustrate an intramedullary nail 100 where the transition section 104 and the distal section 106 have fins 144. The fins 144 provide rotational resistance for the intramedullary nail 100.

FIGS. 12 and 18 illustrate an intramedullary nail 100 having barbs 142 located on the distal section 106 and a portion of the transition section 104. The barbs 142 provide rotational resistance for the intramedullary nail 100.

Intramedullary nails according to some embodiments of the present invention may be inserted into a patient by any suitable known technique. Generally, the intramedullary canal of the bone is prepared with an appropriate tool to create a void for insertion of the nail. Some portions of the void may be prepared to be about 1 millimeter larger than the perimeter of the nail to permit sufficient space for blood flow after insertion of the nail. A guide pin or wire is optionally inserted into the prepared medullary canal. The nail is then introduced into the desired position. If the nail is cannulated, the nail can be introduced over the guide wire. The position of the nail may be confirmed by image intensification.

Figure 19:
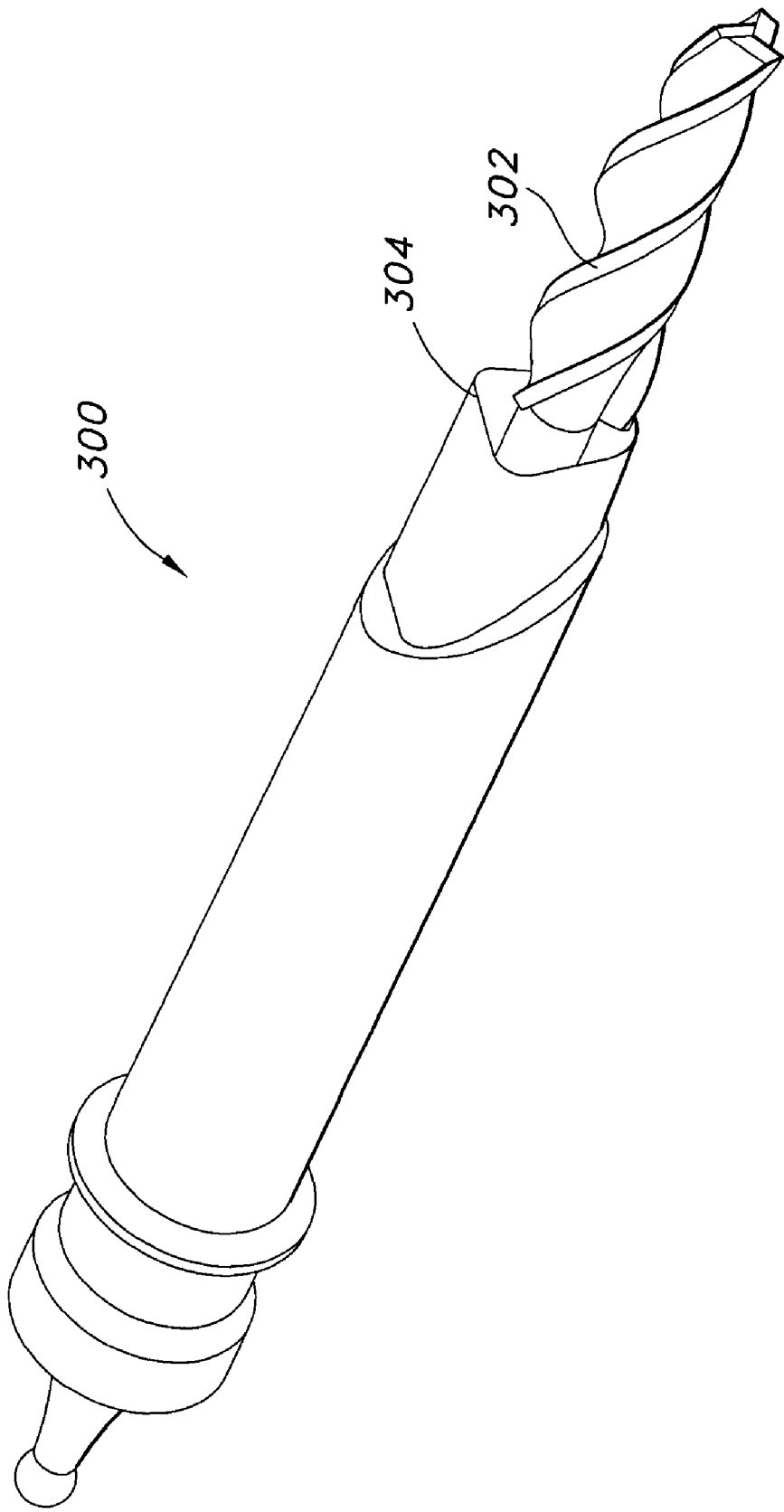
FIG. 19 is a perspective view of a tool according to an embodiment of the present invention for preparing bone to receive certain devices according to certain embodiments of the present invention.

FIG. 19 shows one embodiment of a tool 300 for preparing a medullary canal. The tool has a drill bit 302 for reaming and also a mortise chisel 304. In operation, the drill bit 302 reams out the medullary canal of the femur and the mortise chisel 304 cuts out a larger section in the more proximal end of a bone. As shown in FIG. 19, the mortise chisel 304 has an anatomically derived cross-section of approximately the same shape as the proximal section of the intramedullary nail. By applying this type of shaped, mortise chisel, the proximal end of the nail will be better enabled to seat on cortical bone that has been only minimally altered. The mortise chisel 304 may be of a wide variety of shapes, even complicated, asymmetrical shapes. This is advantageous because it enables a device and method for preparing voids able to accept a wide variety of shapes of intramedullary nails without merely over-reaming circular voids. Preparation of an accurately conforming void is valuable in avoiding unnecessary removal of healthy bone, and in ensuring stable seating of the nail.

In operation, the tool 300 of the embodiment shown is advanced as a unit, with the drill bit 302 reaming and the mortise chisel 304 cutting simultaneously. The drill bit 302 may be turned with a power driver, or by hand. Likewise, the entire tool 300 may be advanced into a medullary canal manually, or advanced with the assistance of mechanical advantage or power equipment. In other configurations, the drill bit 302 may be cannulated (not shown) such that the entire tool 300 is operable over and guided by a guide wire that has been inserted into the medullary canal.

In other embodiments, the bit for reaming is a more traditional reamer that is separate from a cutting tool such as the mortise chisel 304. The method for preparing a void in such an instance would include first reaming an opening with a traditional reamer. A device such as a chisel or a broach, shaped similar to the intramedullary nail to be implanted, would then be used to prepare the void. The chisel or broach may be driven in by hand, with the assistance of a hammer or mallet, or with the use of other power equipment. A nail consistent with the void prepared would then be implanted.

Other custom instruments such as a contoured broach or a custom router bit and template could be used as well. Broaches have long been used to prepare openings for hip stems, and the use of a broach would be familiar to one of skill in the art. A router bit and template could be use, in effect, to mill out the desired shape in the bone. Such a method might also be used in combination with reaming or broaching to create the desired void.

Intramedullary nails in accordance with some of the embodiments of the present invention may be used to treat proximal femoral fractures and femoral shaft fractures, among other fractures of long bones and other bone maladies. When used to treat femoral shaft fractures, the intramedullary nail is secured in the femur by one or more fastening devices. When used for the treatment of proximal femoral fractures the intramedullary nail is preferably used in conjunction with a fastening assembly.

Figure 20:
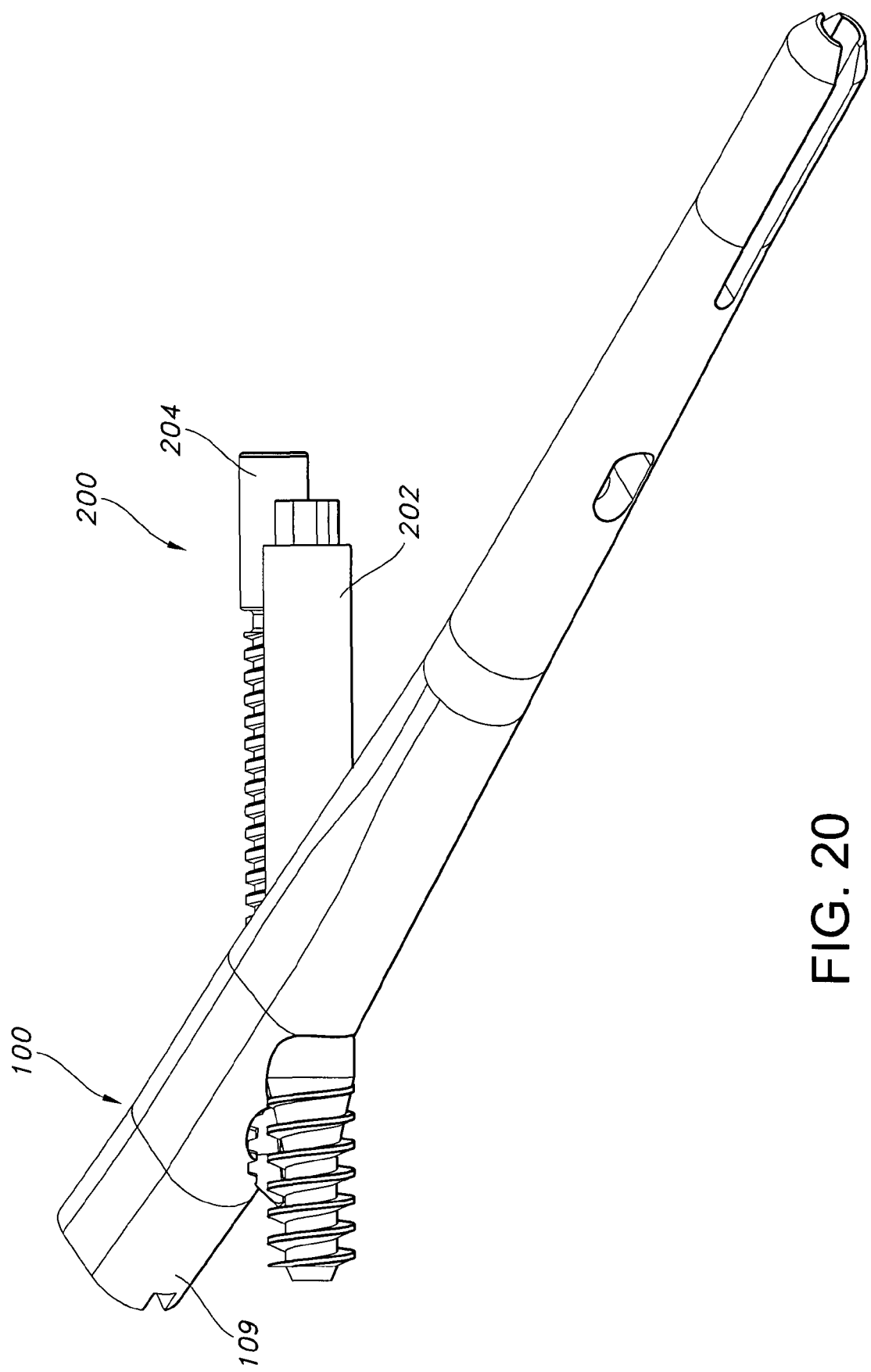
FIG. 20 is a perspective view of a device which includes a version of a fastener assembly according to one embodiment of the present invention.
Figure 21:
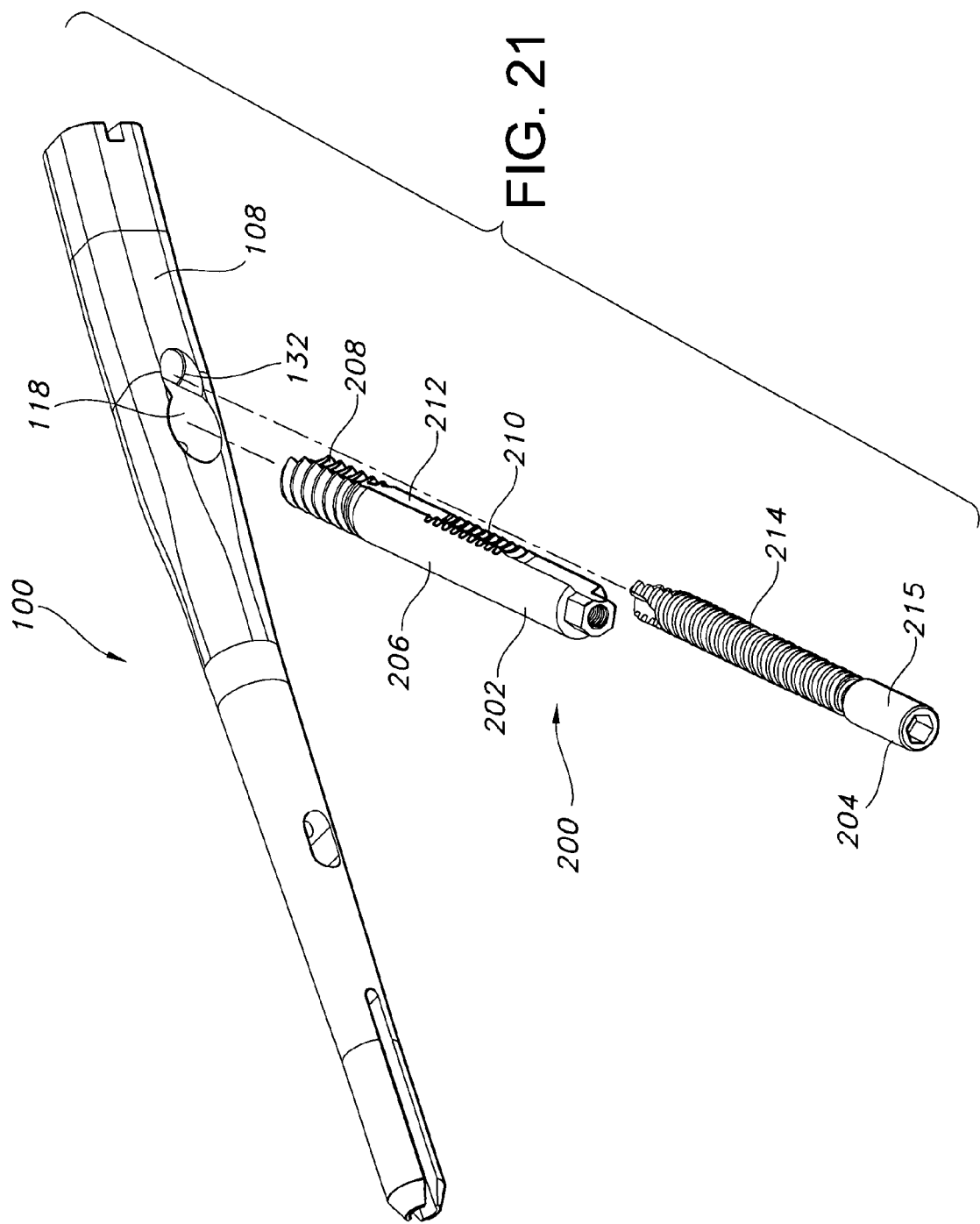
FIG. 21 is an exploded view of the intramedullary device and fastener assembly shown in FIG. 20.
Figures 22, 23:
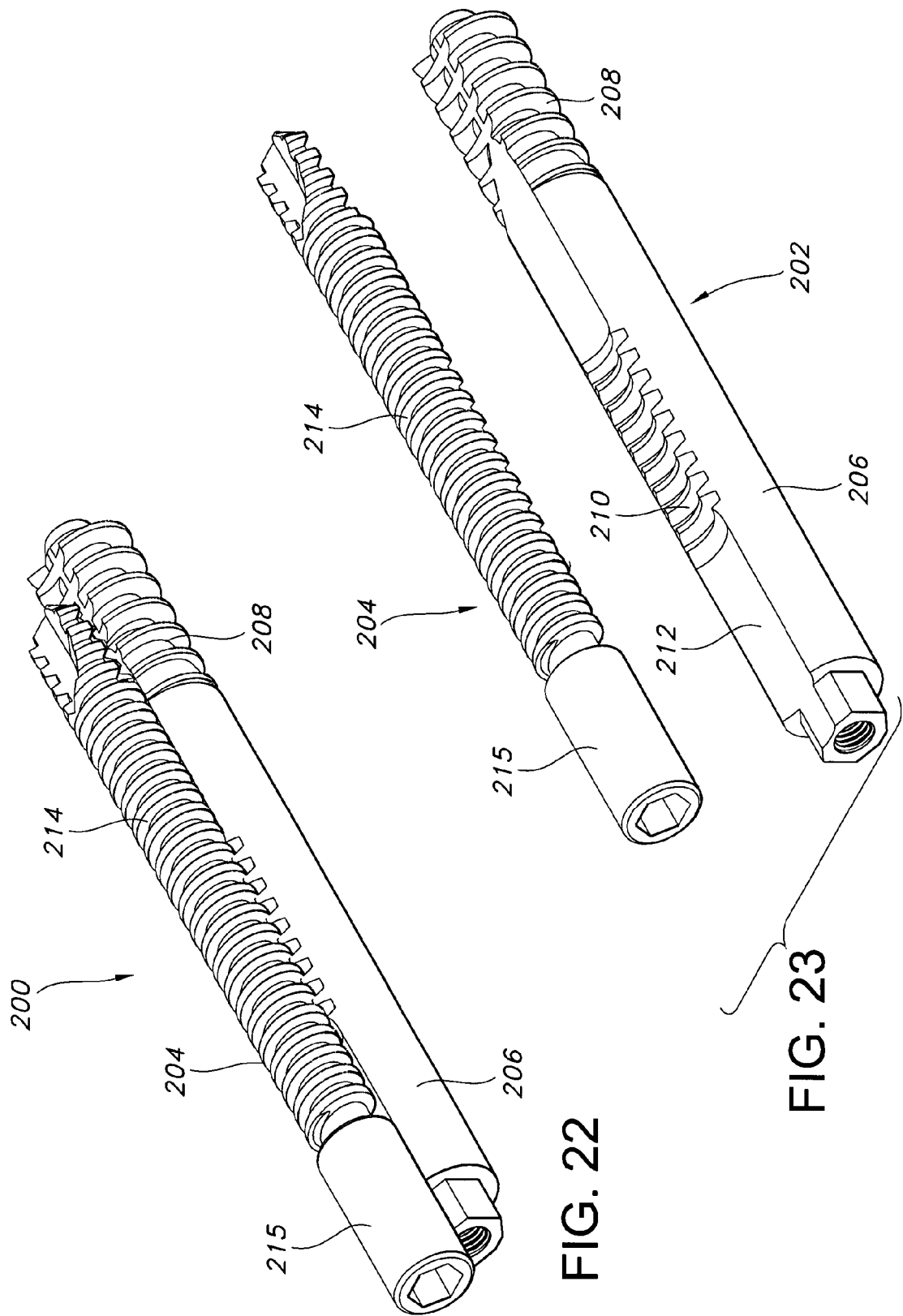
FIG. 22 is a perspective view of the fastener assembly shown in FIG. 20.
FIG. 23 is an exploded view of the fastener assembly of FIG. 20.
Figure 29:
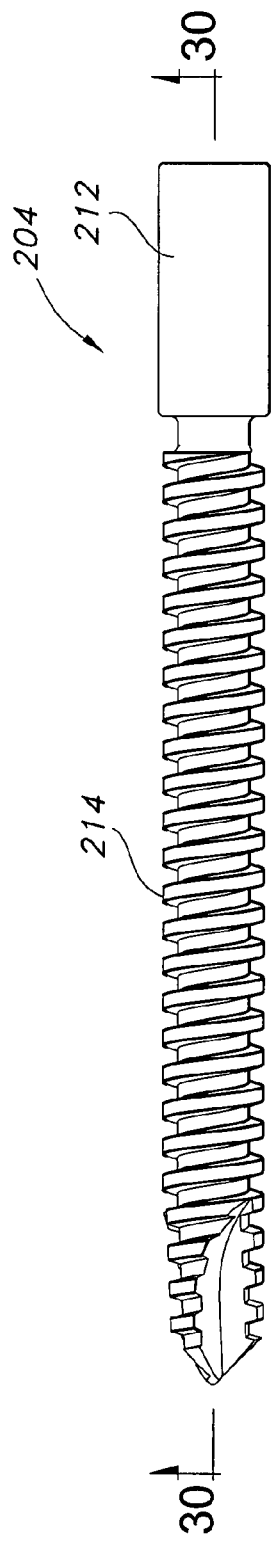
FIG. 29 is an elevation view of the compression device of the fastener assembly of FIG. 22.
Figure 30:
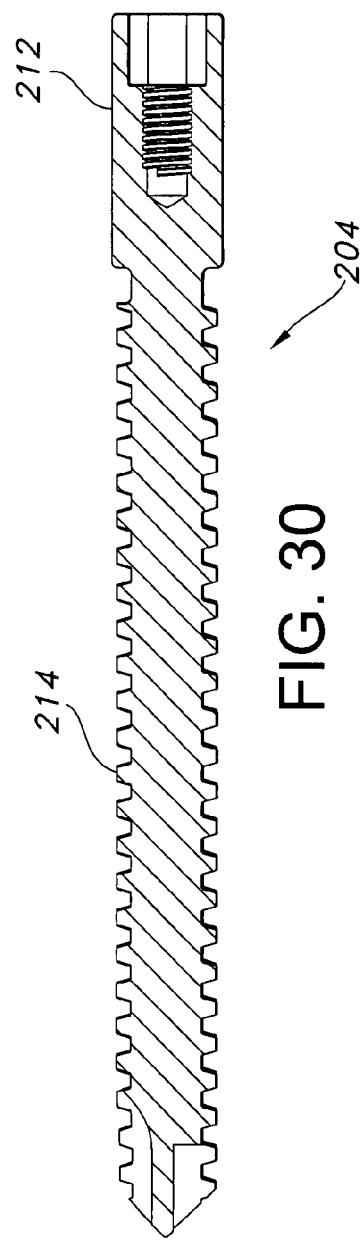
FIG. 30 is a cross-section view of the compression device of FIG. 29 shown through line 30-30.
Figure 31:
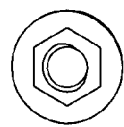
FIG. 31 is an end view of one end of the compression device of FIG. 29.
Figure 32:
FIG. 32 is an end view of the other end of the compression device of FIG. 29.

FIGS. 20 and 21 illustrate an intramedullary nail 100 according to one embodiment of the present invention used in conjunction with a fastening assembly 200 according to one embodiment of the present invention. This type of fastening assembly may be used in a variety of bones and to treat a number of indications, but for the purpose of providing an example, it is being described here in use with the proximal femur. In general, the fastening assembly is useful in any situation where one fragment of a bone is to be drawn back toward or pushed away from another fragment of the bone in a controlled manner. The fastening assembly provides the additional advantage of being configurable to allow sliding of the assembly in a desired direction after the movement of the bone fragments has been accomplished.

As shown in FIG. 21, the axis of the proximal transverse aperture 118 in the intramedullary nail 100 is angled relative to the proximal section 102 and in use, is directed towards the femoral head. In this embodiment of the fastener assembly 200, an engaging member such as a lag screw 202 is used in conjunction with a compression member, such as a compression screw 204 or a compression peg. The screws are configured such that when in use the circumference of the lag screw 202 partially intersects with the circumference of the compression screw 204, so that the compression screw 204 nests partially within the circumference of the lag screw 202. This particular combination of lag screw 202 and compression screw 204 are further illustrated in FIGS. 22 through 32. Briefly, the lag screw 202 shown in these figures is intended to engage the femoral head and to slide in the transverse aperture 118 of the nail 100. The compression screw 204 engages a shoulder or other structure in transverse aperture 118 and also threads in the portion of lag screw 202 within which compression screw 204 nests, so that rotation of compression screw 204 controls sliding of the lag screw 202 relative to the nail 100 and thus compression of the femoral head against the fracture site.

The lag screw 202 shown in these drawings includes an elongate body 206 and threaded end 208. As shown in FIGS. 24 and 25, the threaded end 208 does not include a sharp end, which reduces the possibility of cut out through the femoral head. The elongate body 206 includes a channel 212 that allows for the positioning of the compression screw 204 partially inside the circumference of the lag screw 202. The channel 212 includes a threaded portion 210 that compliments and cooperates with a threaded section 214 of the compression screw 204. The compression screw 204 includes a threaded section 214 and a head section 215. The threaded section 214 of the compression screw 204 is configured such that the threads are relatively flat and smooth at the exterior surface so that they can easily slide in the aperture and also reduce the possibility of cut out.

The lag screw 202 is received in the proximal transverse aperture 118 and into a pre-drilled hole in the femur so that the lag screw 202 extends across the break and into the femoral head. The threaded end 208 of the lag screw 202 engages the femoral head as the lag screw 202 is rotated within aperture 118, causing its threaded end 208 to engage the femoral head. The threaded end 208 may be any device for obtaining purchase in the femoral head, and includes, but is not limited to, threads of any desired configuration including helices, barbs, blades, hooks, expanding devices, and the like. The placement depth of the lag screw 202 into the femoral head differs depending on the desired compression of the fracture.

The compression screw 204 can also be received through the proximal transverse aperture 118 into a predrilled hole in the femoral head. The threaded section 214 of the compression screw 204 engages with the threaded portion of the channel 212 of the lag screw 202. The proximal transverse aperture 118 has an interior shoulder 132 (FIG. 21) to limit the sliding of the compression screw 204 in the general medial direction and, therefore, the lag screw 202, through the aperture 118. When the compression screw 204 is tightened, the compression screw threads 214 engage with the lag screw channel threaded portion 210 and the compression screw 204 moves in the generally medial direction down the lag screw 202. The head section 215 of the compression screw 204 engages the shoulder 132 of the proximal transverse aperture 118 preventing the compression screw 204 from moving further in the general medial direction. As the compression screw 204 is tightened, the lag screw 202 is drawn in the general lateral direction toward the intramedullary nail compressing the fracture. The compression screw 204 partially intersecting the circumference of the lag screw 202 provides greater surface resistance and aids in the prevention of femoral head rotation. The compression screw 204 therefore acts not only as a part of the mechanism for moving fragments of the fractured bone relative to one another, but also directly contacts bone of the femoral head to help prevent the femoral head from rotating about the axis of the lag screw 202. In other embodiments, it is not necessary to use the compression screw 204 (which may also be referred to as a compression member as discussed below) to compress the fracture, and the fracture may be stabilized simply by installing the compression screw 204 and lag screw 202 (which may also be referred to as an engagement member as discussed below).

In one embodiment, a set screw (not shown), positioned in the proximal end aperture 128 of the intramedullary nail, is used to engage the compression screw 204 and fix the compression screw 204 and lag screw 202 in place. The use of the set screw to fix the fastener assembly 200 in place may be fracture pattern dependent. If a set screw is not used to engage the fastener assembly, the fastener assembly 200 can slide within the proximal aperture limited by the shoulder 132.

In the embodiment of the lag screw and compression screw shown in FIGS. 20-32, the diameter of the compression screw 204 is smaller than the diameter of the lag screw 202. In other embodiments, the diameters of the lag screw and compression screw could be the same or the diameter of the lag screw could be smaller than the diameter of the compression screw. The threads of the lag screw and the compression screw could be a variety of different shapes as known to those skilled in the art. In general, the purpose of the lag screw is to obtain purchase in bone, and the purpose of the compression screw is to engage with and draw or move the lag screw. Any configuration that permits these functions is within the scope of the invention.

The fastener assembly 200 shown in the Figures could additionally be configured to allow the addition of a prosthetic femoral head and neck. In such an embodiment, the lag screw 202 would be replaced with a prosthetic head and neck. The neck would fit into the proximal transverse aperture 118 in the nail 100. The design would be beneficial where degeneration or re-injury of a repaired femoral fracture and hip joint later necessitated a total hip arthroplasty (THA). The decision to accomplish a THA could be made interoperatively, or after some period of time. Instead of having to prepare a femur to accept a hip stem as is known in association with THA, only a small portion of bone would need to be removed, along with the fastener assembly 200. The prosthetic head and neck could then be inserted into the proximal transverse aperture 118, the acetabulum prepared, and the remainder of the THA completed.

FIG. 33 is a cross-section view of an intramedullary nail 100 according to another embodiment of the invention with an alternate fastener assembly 400. The fastener assembly illustrated is very similar to the compressing fastener assembly of Smith & Nephew's IMHS® system, as is more thoroughly disclosed in U.S. Pat. No. 5,032,125 and various related international patents. The improvement of the device illustrated is that it includes the intramedullary nail 100 with an anatomically derived shape and its multiple advantages as discussed above. In operation, a sleeve 401 fits through the intramedullary nail 100, and may be secured to the nail by set screw, or other effective mechanisms. A sliding lag screw 402 is able to move axially within the sleeve 401. A compressing screw 404 is threaded into the sliding lag screw 402 such that tightening of the compressing screw 404 draws the sliding lag screw 402 back into the sleeve 401. With this mechanism, a bone fragment may be brought into a desired position, but still permitted to achieve sliding compression once positioned.

FIGS. 34-35 illustrate a fastener assembly 200 according to another embodiment of the invention having a lag screw 202 and a compression peg 502. As shown in FIG. 34, the lag screw 202 and the compression peg 502 are configured such that, when in use, the circumference of the lag screw 202 partially intersects with the circumference of the compression peg 502, although in some embodiments the circumferences might be adjacent rather than intersecting. The lag screw 202 includes an elongate body 206 and threaded end 208. The lag screw 202 has a key 504 on the channel 212. The compression peg 502 has a slot 503 that is adapted to receive the key 504 of the lag screw 202. The key 504 and slot 503 can be a variety of complimentary shapes, such as, when considered in cross section, triangular, D-shaped, key-holed and other shapes as are apparent to those skilled in the art. In operation, the compression peg 502 may be moved relative to the lag screw 202 by a compression tool (not shown) that applies disparate forces between the compression peg 502 and the lag screw 202, or between the entire assembly and the intramedullary nail 100.

In the fastener assembly 200 shown in FIGS. 34-35, the lag screw 202 is received to slide in a proximal aperture of the intramedullary nail so that the lag screw 202 extends across the break and into the femoral head. The threaded end 208 of the lag screw 202 engages the femoral head. Once the lag screw 200 has been properly engaged with the femoral head, the compression peg 502 is inserted in the proximal aperture into a predrilled hole in the femoral head, in order to prevent further rotation of the lag screw 202 as the slot 503 of the compression peg 502 receives the key 504 of the lag screw 202. By providing more area for resistance, the compression peg 502 helps to prevent the rotation of the femoral head on the lag screw 202. The compression peg 502 is fixed in position in the intramedullary nail 100 by a set screw positioned in the proximal end aperture of the nail. The lag screw 202 can slide on the compression peg 502 through the proximal aperture. In another embodiment, the compression peg 502 has barbs on its surface.

A fastener assembly 200 according to another embodiment of the invention is illustrated in FIGS. 36-37. The fastener assembly 200 of this embodiment has a compression peg 502 and a lag screw 202 similar to the embodiment illustrated in FIGS. 34-35, except that the key 504 of the lag screw 202 and the slot 503 of the compression peg 502 have complimentary ratchet teeth 506. The compression peg 502 is fixed in position in the intramedullary nail by a set screw positioned in the proximal end aperture. Compression of the fracture can be achieved by pulling the lag screw in the general lateral direction. The ratchet teeth 506 allow the lag screw 202 to move in the general lateral direction, but prevent the lag screw 202 from moving in the general medial direction. A compression tool similar to the tool described in association with FIGS. 34-35 may be used to accomplish the movement.

FIGS. 38-39 show a fastener assembly 200 according to another embodiment of the invention having a lag screw 602, a cross hair screw 610 and a compression screw 604. The lag screw 602 includes an elongate body 606 and threaded end 608. The elongate body 606 is semi-circular shaped in cross section. The screws 602, 604, 610 are configured so that the circumference of the lag screw 602 intersects with the circumferences of the cross hair screw 610 and the compression screw 604. The elongate body 606 of the lag screw 602 is threaded to compliment and cooperate with a threaded section 602 of the cross hair screw 610. The cross hair screw 610 is threaded to engage with the lag screw 602 and the compression screw 604. The compression screw 604 includes a threaded portion 614 and a head portion 612.

In this embodiment, the lag screw 602, the cross hair screw 610 and the compression screw 604 are received simultaneously to slide in a proximal aperture of an intramedullary screw. The lag screw 602 extends across the break and into the femoral head. The threaded end 608 of the lag screw 602 engages the femoral head. As compression screw 604 is tightened, the threads 614 of the compression screw engage the threads of the cross hair screw 610 and lag screw 602, thereby moving the lag screw 602 in the general lateral direction toward the intramedullary nail providing compression to the femoral head. The cross hair screw 610 is then turned causing the compression screw 604 to move in the distal direction away from the lag screw 602. The fastener assembly 200 can alternatively be configured so that the compression screw 604 moves proximally relative to the lag screw 602. The compression screw 604 separates from the lag screw 602 to help to prevent rotation of the femoral head on the lag screw 602 by adding more area for resistance.

FIGS. 40-41 illustrate a fastener assembly 200 according to another embodiment of the invention having a lag screw 702 and a compression peg 704. The lag-screw 702 includes an elongate body 706 and a threaded end 708. The elongate body 706 is semi-circular shaped in order to allow the compression peg 704 to be positioned partially inside the circumference of the lag screw 702 for insertion into the femur and has a key 712 positioned on the interior side of the elongate body 706. The elongate body 706 also has an aperture 710 through the body. The compression peg 704 is generally cylindrical and is sized to fit within the semi-circular body 706 of the lag screw. The key 712 of the lag screw is received by a slot 714 in the compression peg 704. The key 712 and slot 714 contain complimentary ratchet teeth (not shown).

In this embodiment, the lag screw 702 and the compression peg 704 are received simultaneously to slide in a proximal aperture of an intramedullary nail into a pre-drilled hole in the femur. The lag screw 702 extends across the break and into the femoral head. The threaded end of the lag screw 702 engages the femoral head. A compression tool similar to the tool describe in association with FIGS. 34-35 may be used to accomplish movement between the compression peg 704 and the lag screw 702, or between the entire assembly and the intramedullary nail 100. A set screw may used to fix the position of the fastener assembly. The set screw is configured such that when the set screw is tightened a protrusion on the set screw is received through the slot 710 of the lag screw 702 and moves the compression screw 704 away from the lag screw 702. The compression screw 704 separate from the lag screw 702 helps to prevent rotation of the femoral head on the lag screw by adding more area for resistance.

Figure 42:
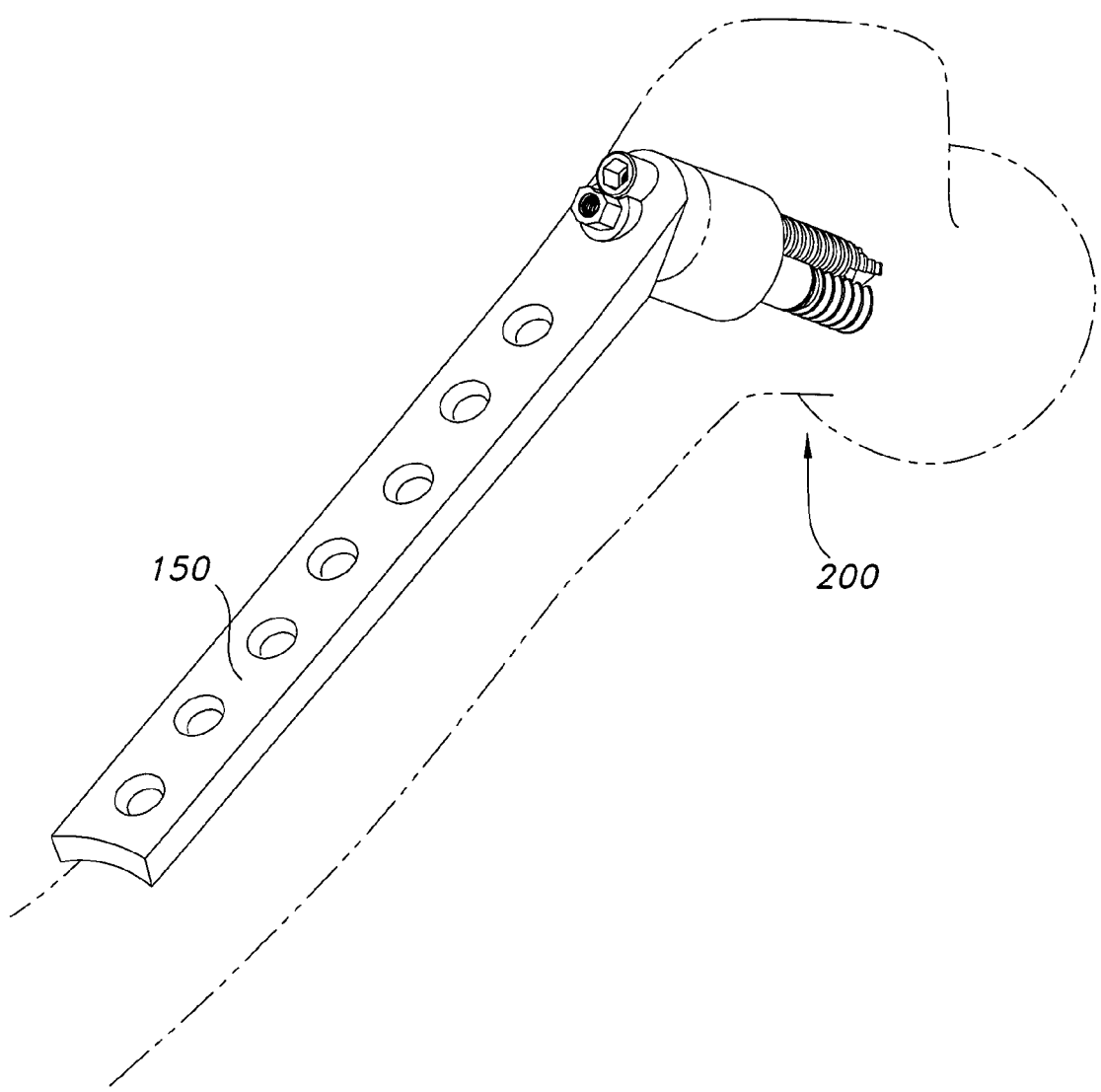
FIG. 42 is a perspective view of a compression plate according to an embodiment of the present invention which includes a fastener assembly according to an embodiment of the invention.

FIG. 42 illustrates another embodiment of the invention where a fastener assembly 200 is employed in cooperation with a compression plate 150. As illustrated, the devices are being applied to a femur. The various embodiments of the fastener assembly 200 disclosed above may be used with a similar compression plate, and various compression plates may be configured to be applicable to other parts of the anatomy.

Figure 43:
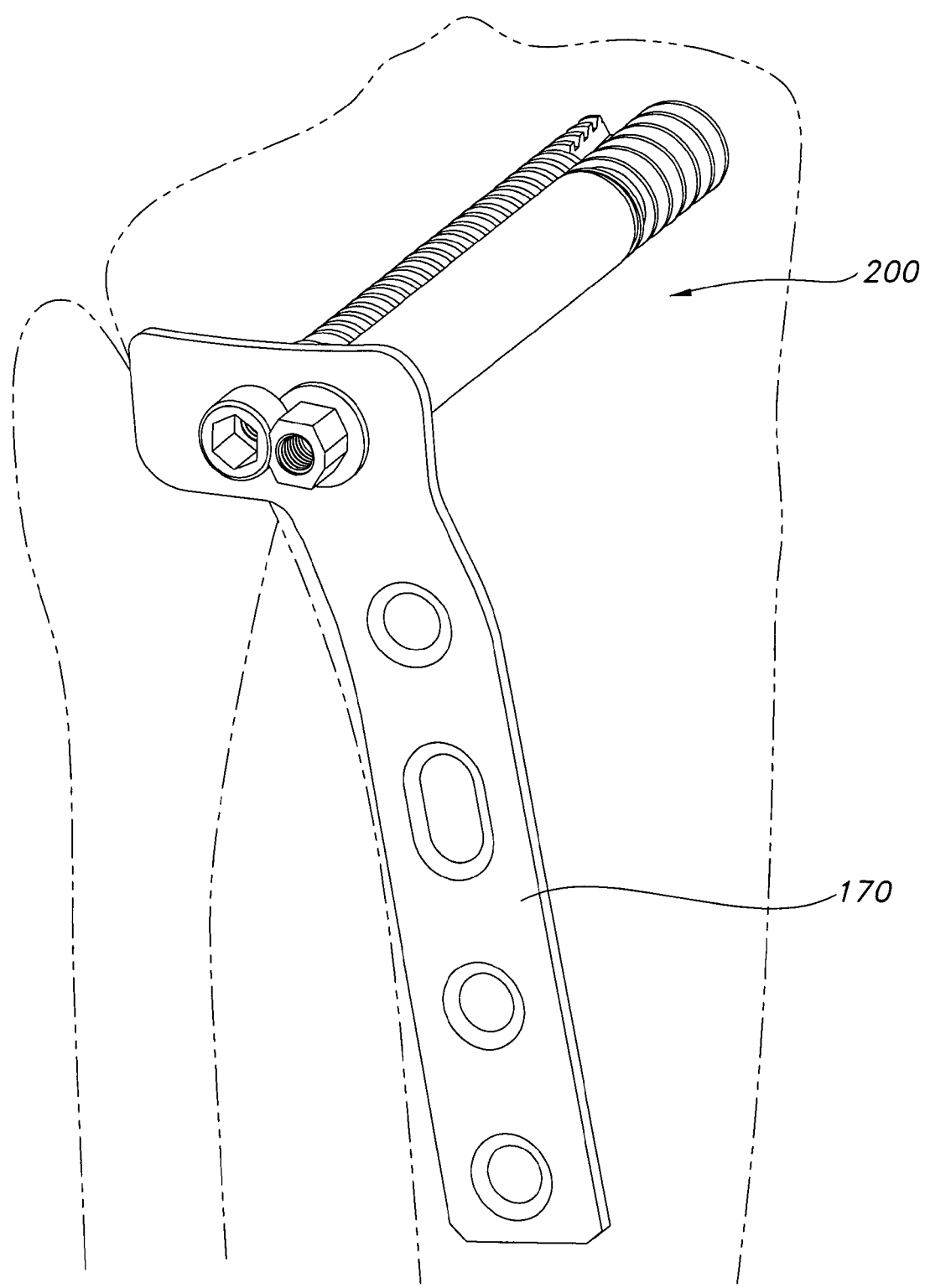
FIG. 43 is a perspective view of a periarticular plate according to an embodiment of the present invention which includes a fastener assembly according to an embodiment of the invention.

FIG. 43 illustrates another embodiment of the invention where a fastener assembly 200 is being used with a periarticular plate 170. The plate and fastener assembly shown are being applied to a proximal tibia. The various embodiments of the fastener assembly 200 disclosed above may be used with a similar periarticular plate and various periarticular plates may be configured to be applicable to other parts of the anatomy.

Figure 44:
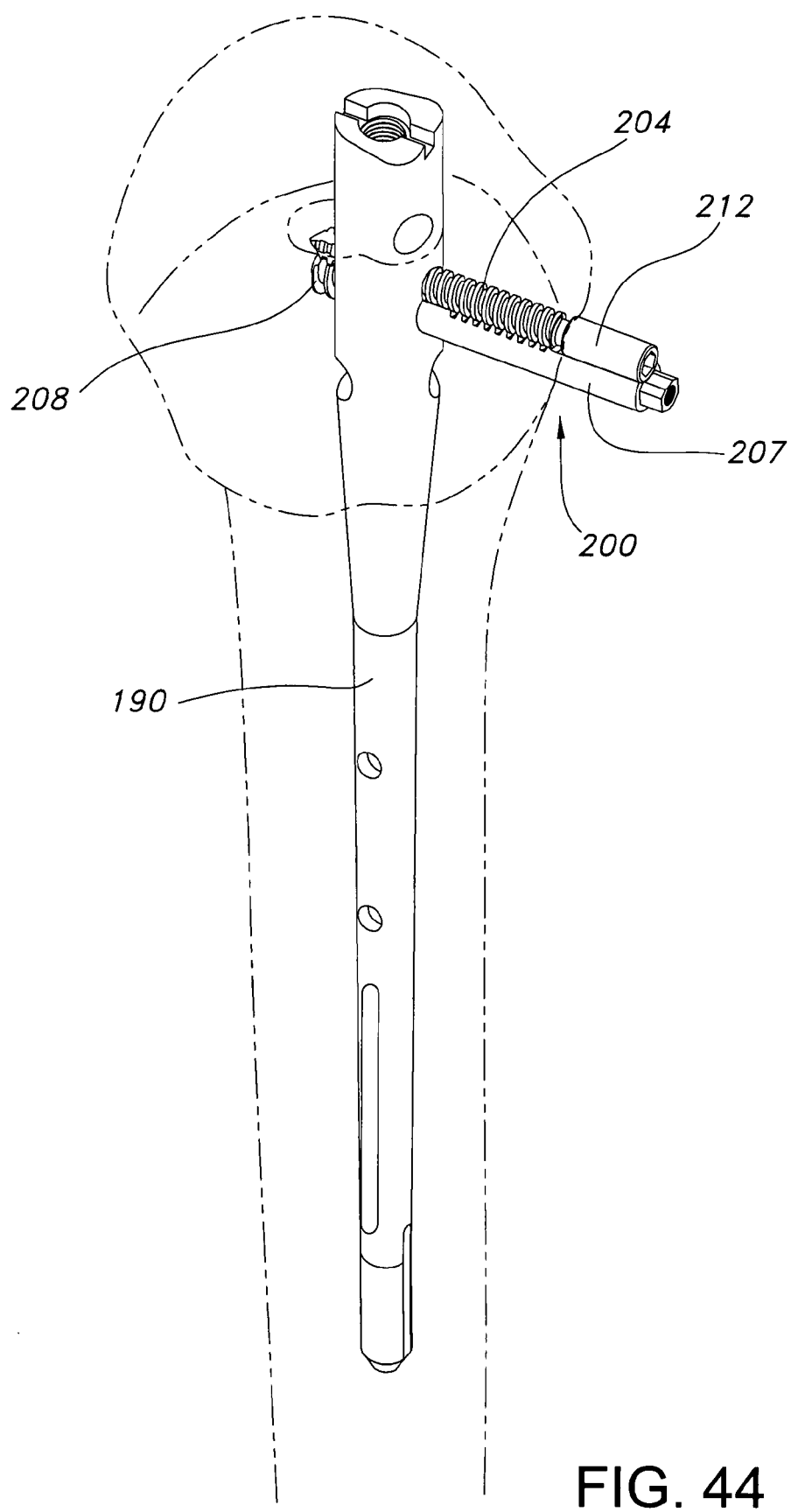
FIG. 44 is a perspective view of a device according to an embodiment of the present invention used in the context of humeral repair in a shoulder joint.

FIG. 44 illustrates another embodiment of the invention where a fastener assembly 200 is used in combination with a humeral nail 190. As illustrated, a head section 212 of compression screw 204 bears against the humerus to draw compression against the humerus. With the compression force applied to lag screw 202, and the lag screw 202 affixed to a bone fragment through its threaded end 208, the bone fragment may be drawn into position for proper healing. In some circumstances, it may be advantageous to place a washer or bearing surface (not shown) between the head section 212 and the humeral bone against which the head section 212 compresses. In yet another variant, the opening in the humerus may be enlarged such that head section 212 is permitted to penetrate the humerus and bear against a portion of the humeral nail 190. In such an embodiment, the fastener assembly 200 would be shorter than illustrated in FIG. 44 to obtain purchase in the same area of bone with the threaded end 208. The various embodiments of the fastener assembly 200 disclosed above may be used with a similar nail and various nails may be configured to be applicable to other parts of the anatomy.

FIGS. 45-60 show apparatuses 2000 for treating bone maladies in accordance with other embodiments of the present invention. The apparatuses 2000 shown in these figures generally include a stabilizing structure 2002 and a fastening assembly 2004. The stabilizing structure 2002 shown in FIG. 45 is a bone plate, however, in other embodiments, stabilizing structure 2002 may be other orthopaedic devices for at least partial application to the bony anatomy, such as the outer surface of a bone.

Similar to the intramedullary nails discussed above, the stabilizing structure 2002 may feature geometries that impart a moment of inertia to a cross section of the stabilizing structure 2002 oriented at least partially in the direction of a lateral side or aspect of the stabilizing structure 2002, to increase its strength and/or robustness. For instance, FIG. 45 shows a stabilizing structure 2002 in which the proximal portion has a lateral side with an increased mass to impart additional strength and resistance to tension. In other embodiments, however, such geometries are unnecessary and stabilizing structure 2002 may feature other traditional or non-traditional geometries.

Figure 45:
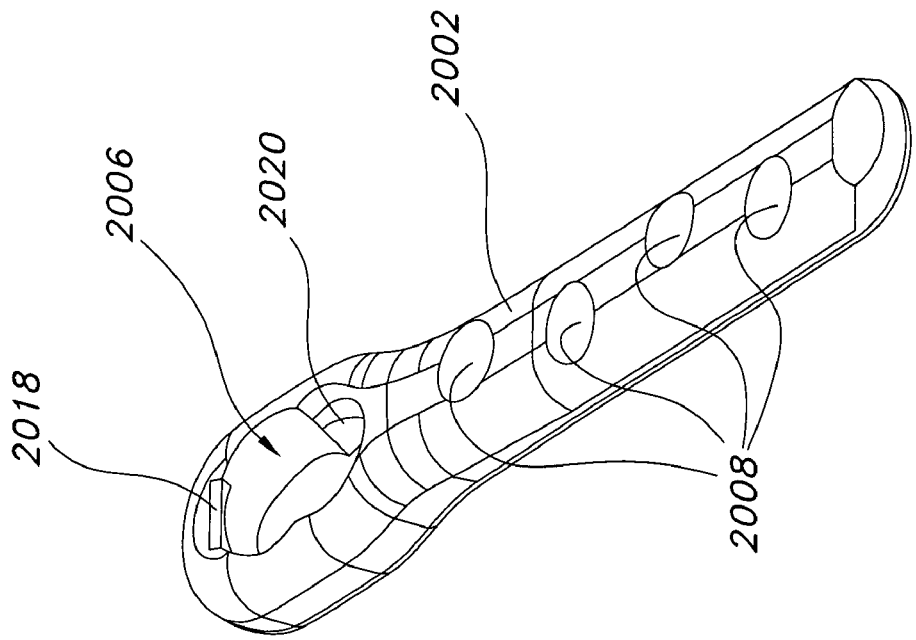
FIG. 45 is a perspective view of a stabilizing structure according to another embodiment of the present invention.

The stabilizing structure 2002 shown in FIG. 45 includes a first transverse aperture 2006 and a number of additional apertures 2008. Transverse aperture 2006 extends through a proximal portion of stabilizing structure 2002, such that it can receive a fastening assembly 2004 and (optionally) an insert 2010, as discussed further below. The transverse aperture 2006 shown in FIG. 45 extends through stabilizing structure 2002 at an angle, such that fastening assembly 2004 will roughly parallel a longitudinal axis of the femoral neck when the stabilizing structure 2002 is applied to the proximal femur in the manner shown in FIGS. 47A and 47B. In other embodiments, however, apparatus 2000 can be used to treat bone maladies associated with other parts of the bony anatomy, and transverse aperture 2006 does not necessarily extend through stabilizing structure 2002 at an angle.

The additional apertures 2008 shown in FIG. 45 may be used in conjunction with bone screws or other types of fastening or anchoring devices to secure the stabilizing structure 2002 to the bony anatomy. As discussed further below, one or more of the additional apertures 2008 may also be used to associate the stabilizing structure 2002 with various instrumentation used to install the apparatus 2000.

Figure 46:
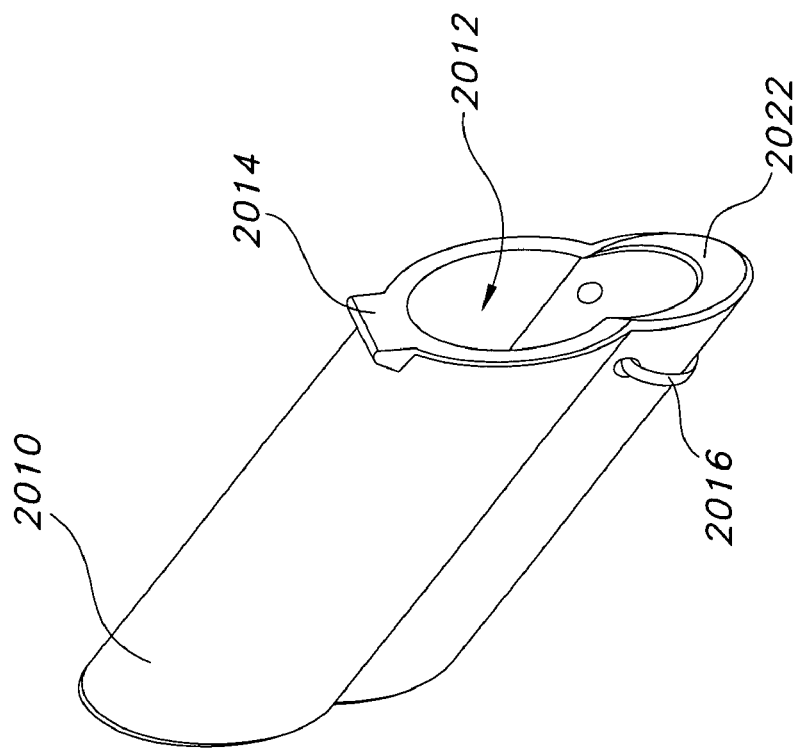
FIG. 46 is a perspective view of an insert that may be used in conjunction with the stabilizing structure shown in FIG. 45.

The transverse aperture 2006 of the stabilizing structures 2002 shown in FIG. 45 may receive an insert 2010 that includes a second transverse aperture 2012, through which the fastening assembly 2004 may pass. One type of insert 2010 is shown in FIG. 46 and includes an arm 2014 and a ridge member 2016 that can interact with indentions/grooves 2018 and 2020 in stabilizing structure 2002 to allow the insert 2010 to be securely snapped into the transverse aperture 2006 in stabilizing structure 2002. In other embodiments, the arm 2014 and ridge member 2016 can extend from stabilizing structure 2002 and the indentions 2018 and 2020 can be located in insert 2010. In some embodiments, ridge member 2016 may be a clip engaged with two apertures extending at least partially into insert 2010, as shown in FIG. 46. In still other embodiments, other structures, devices, and mechanisms can be used to associate insert 2010 with stabilizing structure 2002.

The insert 2010 shown in FIG. 46 also includes a flange 2022 that can interact with one or more portions of the fastening assembly 2004 in a somewhat similar manner to the shoulder 132 discussed in conjunction with the intramedullary nails described above.

The second transverse aperture 2012 shown in FIG. 46 is formed from two overlapping circular apertures, where the distal circular aperture is smaller in diameter than the proximal aperture. In other embodiments, the proximal aperture's diameter may be smaller than the distal aperture's diameter, the apertures may have the same diameter, or the apertures may be formed in other, such as non-circular, shapes.

In some embodiments, the use of a modular insert, such as the insert 2010 shown in FIG. 46, may allow the apparatus 2000 to be installed into a patient using minimally or less invasive techniques, such as, but not limited to, the techniques described further below. For instance, in some embodiments, the use of stabilizing structure 2002 in conjunction with a modular insert 2010, where the stabilizing structure 2002 is installed first and the modular insert 2010 is installed later, may reduce the size of the incision necessary for installation of the apparatus 2000, as opposed to devices that include a one piece structure in the place of the stabilizing structure 2002 and insert 2010.

In these or other embodiments, use of a modular insert 2010 in conjunction with stabilizing structure 2002 may also facilitate a more accurate installation of apparatus 2000. For instance, in some embodiments, stabilizing structure 2002 may be installed prior to certain bone preparation operations, such as drilling cavities necessary for receiving fastening assembly 2004 and/or insert 2010. In such embodiments, the stabilizing structure 2002 may be used to reference and locate various bone preparation operations to facilitate drilling cavities and performing other bone preparation operations accurately with respect to the already installed stabilizing structure 2002.

The fastening assembly 2004 used in conjunction with apparatus 2000 shown in FIGS. 45-61 includes an engaging member 2024 and a compression member 2026. The engaging member 2024 may be positioned above the compression member 2026 (shown in FIG. 47A), below the compression member 2026 (shown in FIG. 47B), or in some other arrangement. Engaging member 2024 can be used to engage a second bone portion, such as the femoral head shown in FIG. 47A. The compression member 2026 may contact and interact with the engaging member 2024 to facilitate a sliding movement of the engaging member 2024 with respect to the transverse apertures 2006 and/or 2012. The compression member 2026 may also at least indirectly interact with the stabilizing structure 2002 to facilitate controlled movement between the bone portions. When apparatus 2000 is used in conjunction with an insert 2010, engaging member 2024 may slide with respect to transverse aperture 2012 (the sliding of which may be controlled by compression member 2026) and a shoulder of compression member 2026 may interact with flange 2022 to limit the depth of insertion of the fastening assembly 2004.

The fastening assembly used in conjunction with stabilizing structure 2002 may be any of the fastening assemblies illustrated in any of the Figures herein, or may be other types of fastening assemblies, and may function and be used in similar manners as the fastening assemblies described above in conjunction with intramedullary nails.

Figure 47A:
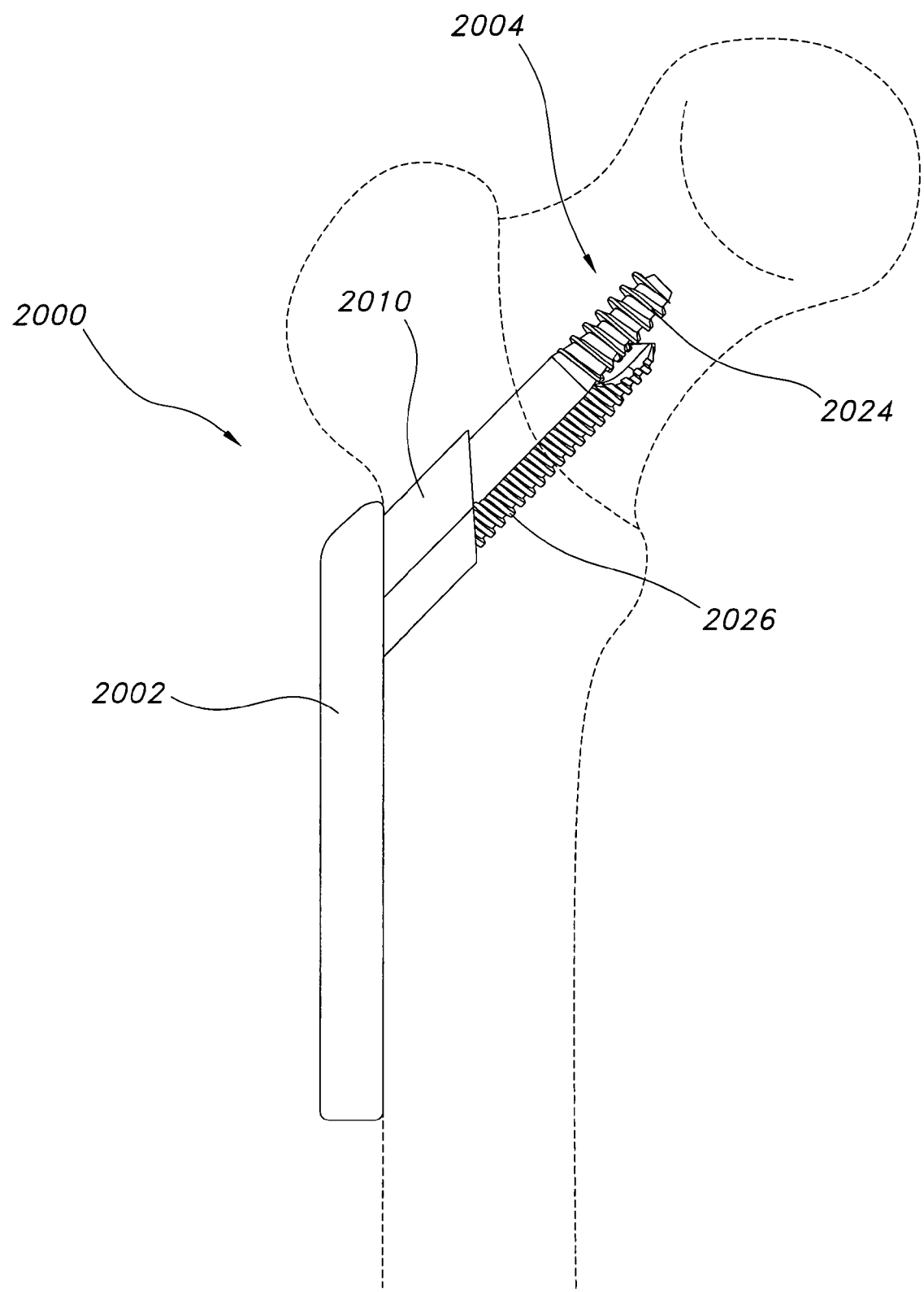
FIG. 47A is a side view of an apparatus for treating bone maladies according to another embodiment of the present invention.
Figure 47B:
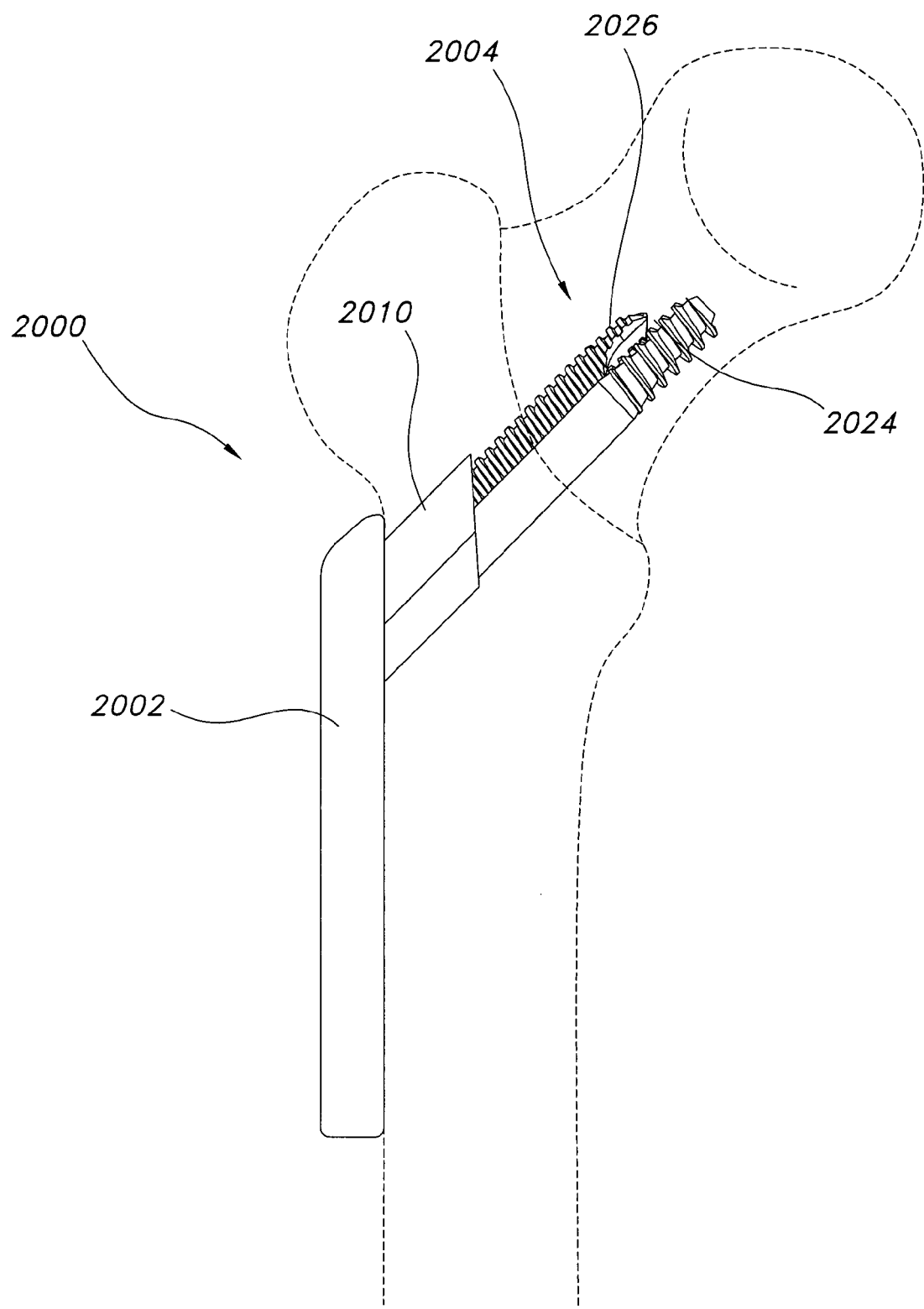
FIG. 47B is a side view of an apparatus for treating bone maladies according to another embodiment of the present invention.

FIGS. 48-60 illustrate instrumentation used in accordance with one method for installing the apparatus 2000 shown in FIG. 47A, although other methods are possible and within the scope of the present invention.

Figure 48:
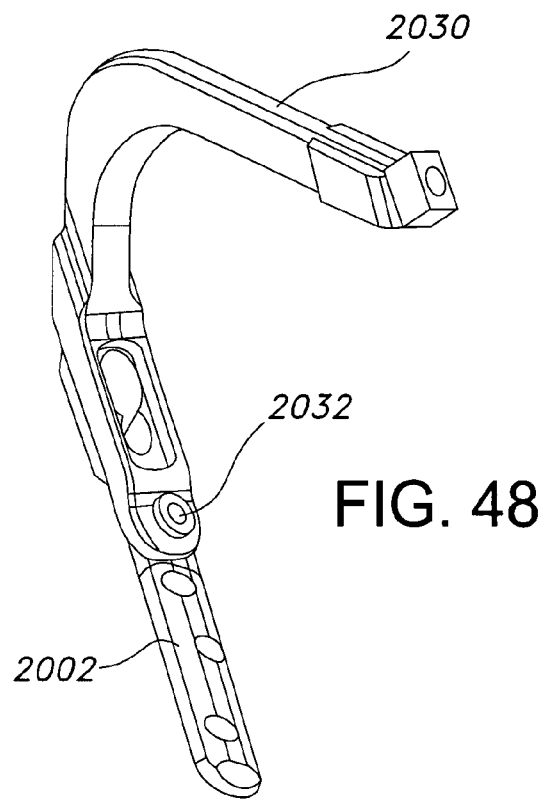

FIG. 48 shows the stabilizing structure 2002 associated with a handle 2030. The handle 2030 can be attached to the stabilizing structure 2002 using a locking post screw 2032 connected to one of the apertures 2008 (such as shown in FIG. 48) or in another manner. Using the handle 2030, the stabilizing structure 2002 may be inserted percutaneously, keeping soft tissue damage to a minimum. Once inserted percutaneously, stabilizing structure 2002 may be secured to an outer surface of the bony anatomy using one or more screws or other fasteners passing through apertures 2008. In other embodiments, stabilizing structure 2002 can be secured to the bony anatomy using screws or other fasteners passing through apertures 2008 at any point during the installation of apparatus 2000.

Figure 49:
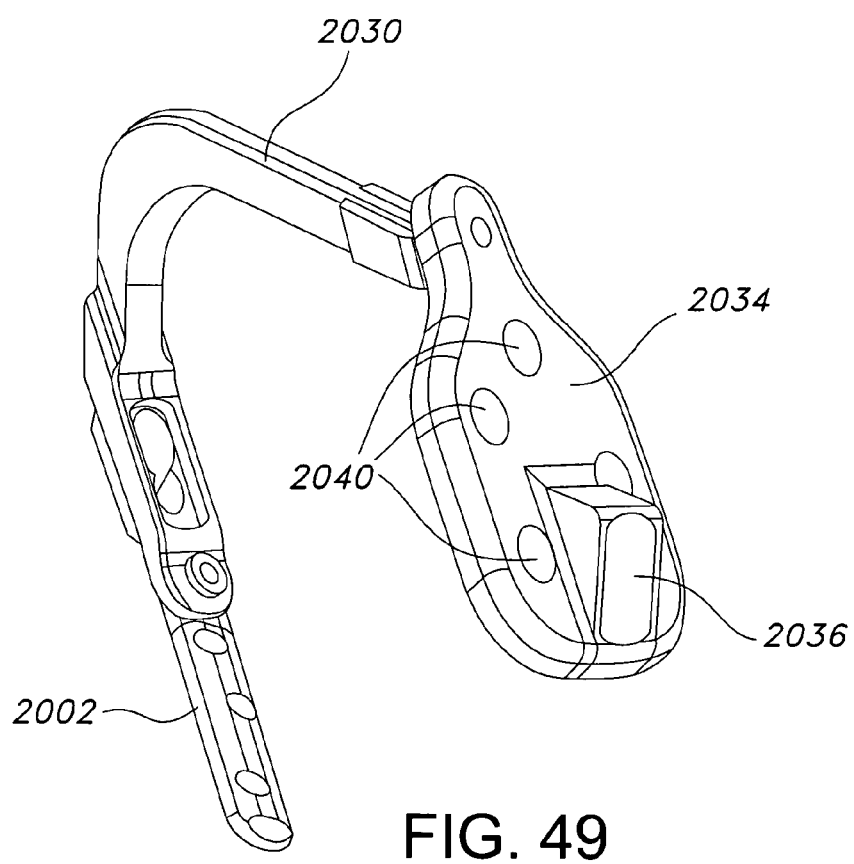
Figure 50:
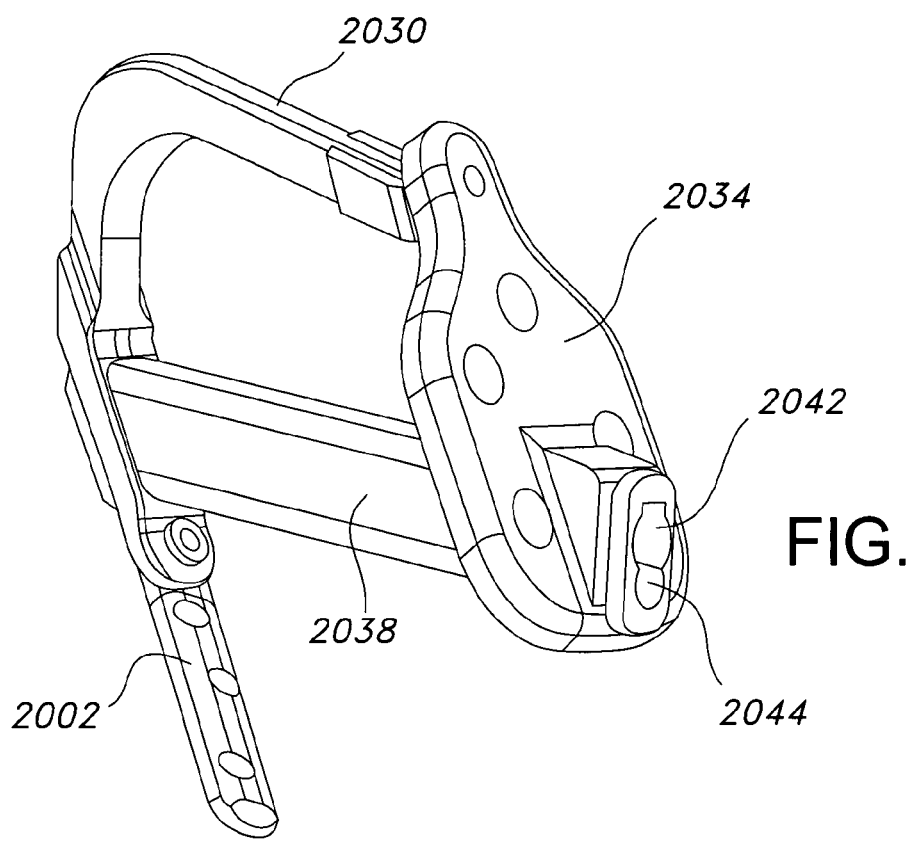

As shown in FIG. 49, the handle 2030 may also receive a targeter 2034. The targeter 2034 shown in FIG. 49 includes an opening 2036 to permit the insertion of a drill sleeve 2038 (as shown in FIG. 50) as well as other apertures 2040 for receiving additional fixation tools, devices or other structures. In other embodiments, targeter 2034 is integral with handle 2030. In still other embodiments, targeter 2034 is not necessary, and drill sleeve 2038 may be positioned with respect to the stabilizing structure 2002 in another manner. For instance, in some embodiments, drill sleeve 2038 is connected to handle 2030 directly, or is formed integrally with handle 2030.

The drill sleeve 2038 shown in FIG. 50 extends through the opening 2036 in the targeter 2034 to approximately the transverse aperture 2006 extending through stabilizing structure 2002. As shown, the drill sleeve 2038 includes first and second tubular portions 2042 and 2044. Tubular portions 2042 and 2044 may receive a wide variety of tools, instruments, and other items.

Figure 51:
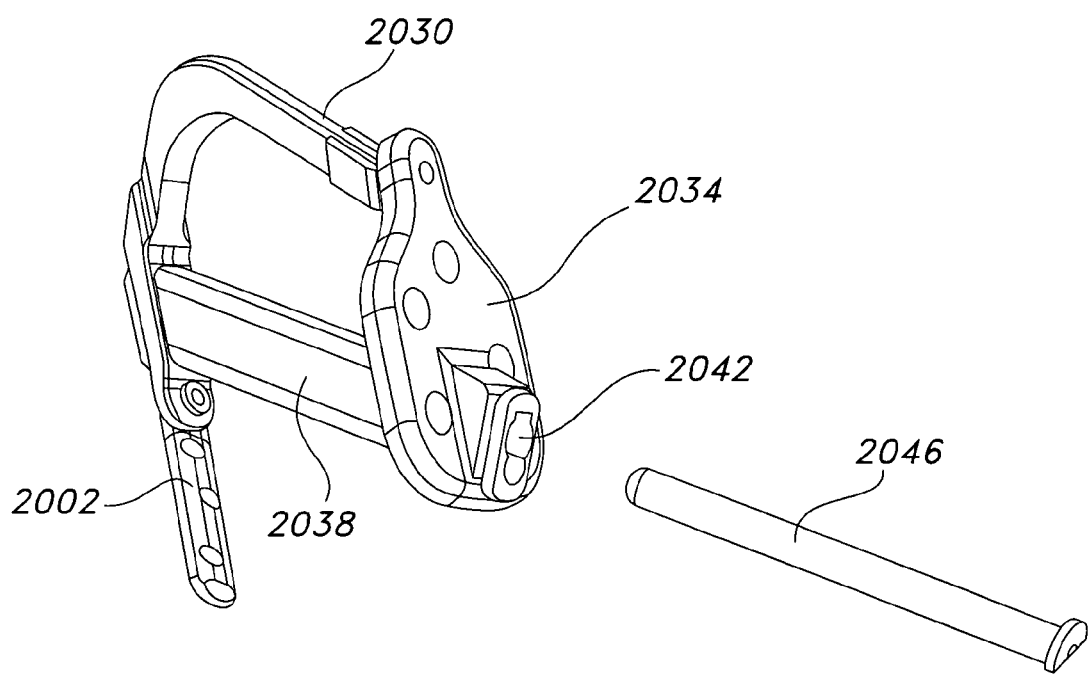
Figure 52:
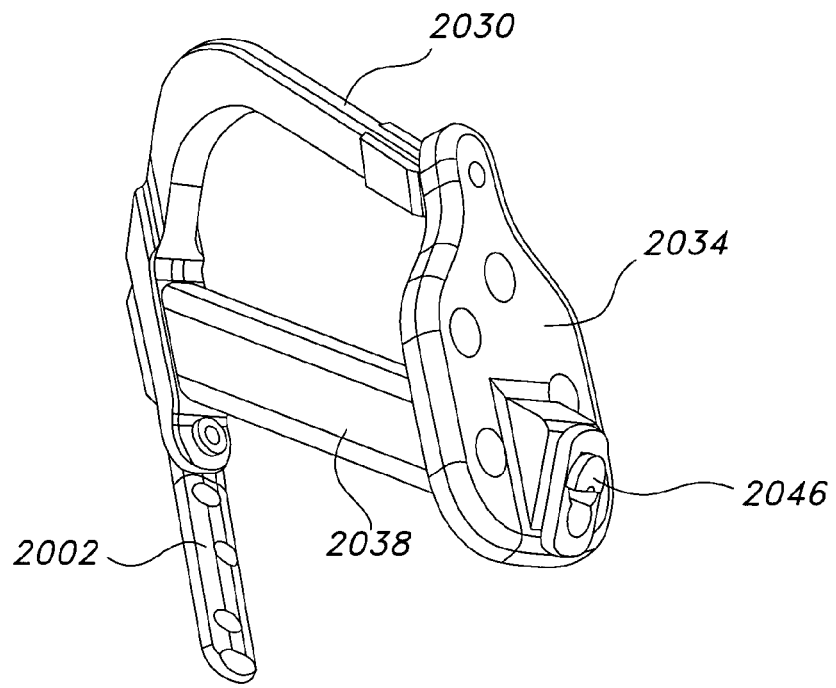

For instance, FIGS. 51 and 52 illustrate the insertion of a guide pin sleeve 2046 into the first tubular portion 2042, which may be cannulated to receive a guide pin (not shown). The guide pin may be used to guide the movement of subsequent instrumentation or other items placed into one or both of the tubular portions 2042 and 2044.

Figure 53:
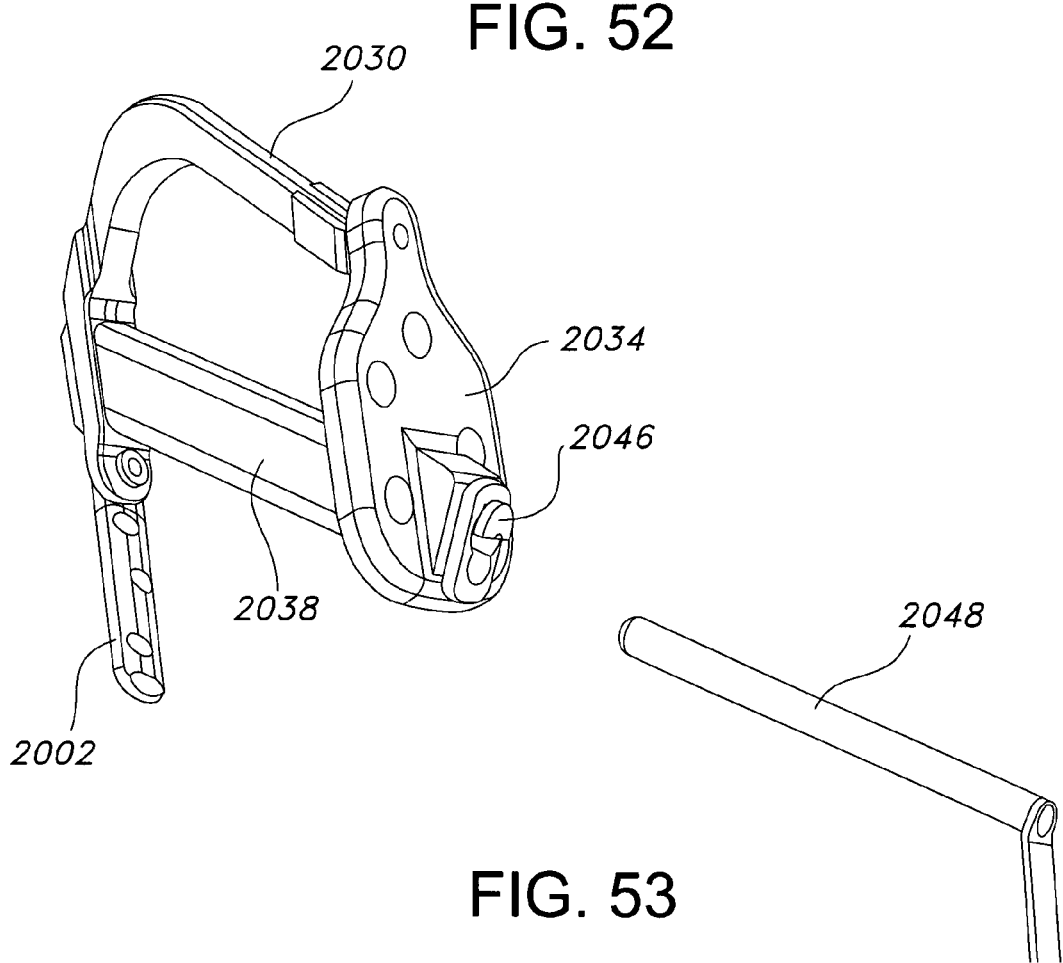
Figure 54:
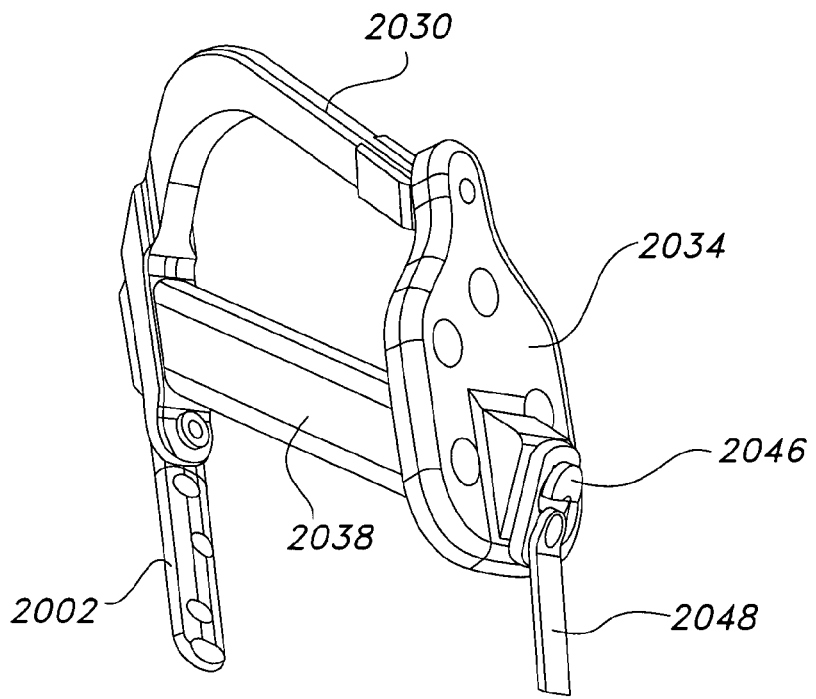
Figure 55:
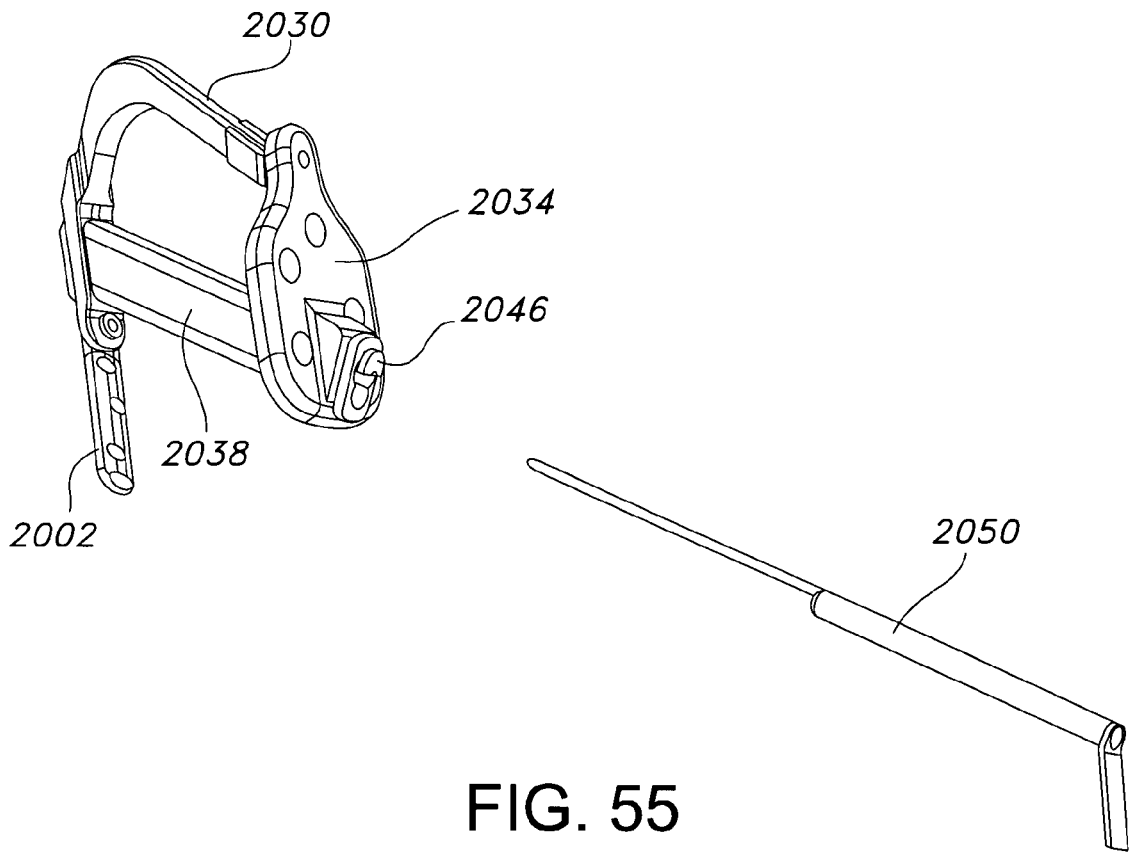

FIGS. 53-54 illustrate the insertion of a compression member drill guide 2048 into the second tubular portion 2044 to guide the movement of one or more drills that will prepare a cavity in the bone for receiving the compression member 2026. Similar instrumentation may be used to prepare another (albeit overlapping in some embodiments) cavity for receiving the engaging member 2024. The same, or different, instrumentation may be used to prepare portions of the drilled cavities to receive the insert 2010 as well. For instance, in some embodiments, there may be four drilling procedures: one to drill a cavity for receiving the compression member 2026, a second to drill a proximal portion of that cavity slightly larger to receive, in part, the insert 2010, a third to drill a cavity for receiving the engaging member 2024, and a fourth to drill a proximal portion of that cavity slightly larger to receive, in part, the other part of the insert 2010 not accounted for by the second drilling operation. The order and number of these drilling procedures are not necessarily important in all embodiments. In some embodiments, it may be desirable to insert an anti-rotation device 2050 (such as shown in FIG. 55) into one or both of the tubular portions 2042 and 2044 to prevent the bone portions from rotating with respect to one another during the drilling procedures.

Figure 56:
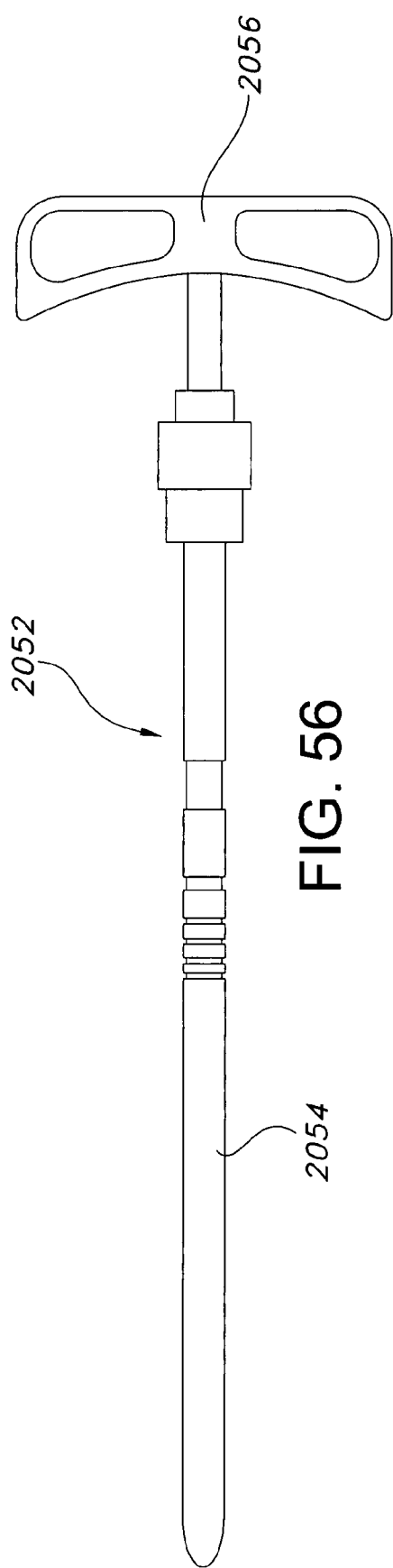
Figure 57:
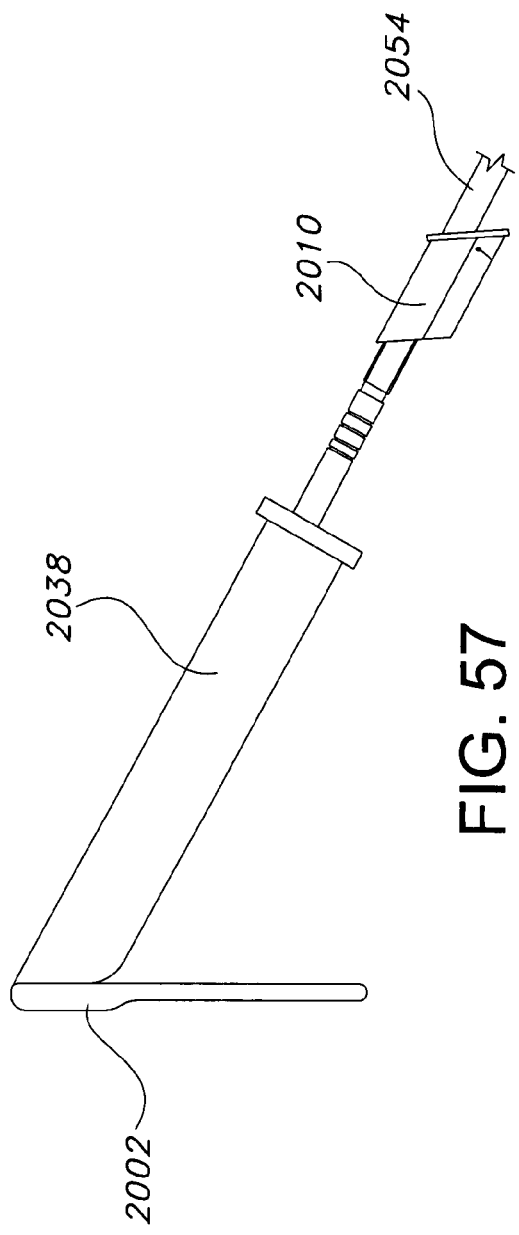
Figure 60:
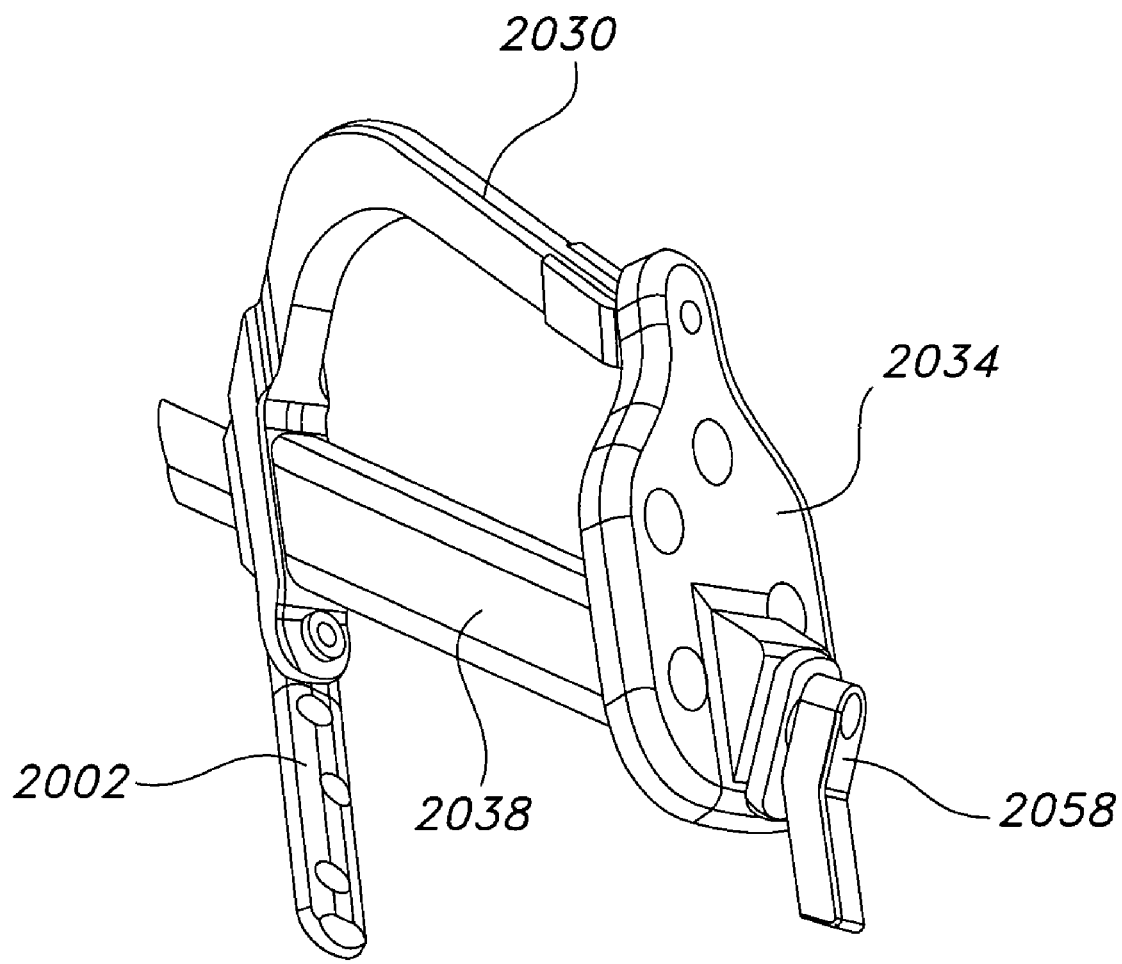

After the cavity for the engaging member 2024 has been prepared, the engaging member 2024 may be inserted using an inserter, such as the inserter 2052 shown in FIG. 56. The inserter 2052 shown in FIG. 56 includes a long cylindrical body 2054 attached to a T-handle 2056. The inserter 2052 may be used to drive the engaging member 2024 into the prepared cavity, and also to rotate the engaging member 2024 to facilitate engaging the bone, such as the femoral head. In some embodiments, the inserter 2052 may be cannulated and include a rod extending along at least a portion of the length of the cannulation, with a threaded tip at its end. This threaded tip may interact with threads (not shown) inside the head of the engaging member 2024 to connect the inserter 2052 to the engaging member 2024. In other embodiments, power tools may be employed to help engage the engaging member 2024 with the bone.

After the engaging member 2024 is installed, as shown in FIGS. 57-60, the T-handle 2056 may be removed and the insert 2010 may be slipped over the cylindrical body 2054 of the inserter 2052 and driven into place using another inserter 2058. The instrumentation may guide the insert 2010 over the engaging member 2024 and into the transverse aperture 2006 of the stabilizing structure 2002. The ridge 2016, arm 2014 and indentations 2018 and 2020 discussed above may allow the insert to be snapped into place in the transverse aperture 2006.

Subsequently, the compression member 2026 may be installed and adjusted (as discussed above for the intramedullary nail, or in other manners) and the various instrumentation may be removed to complete the installation.

In accordance with the above-described, or other, methodologies, an apparatus 2000 may be installed in the following manner. First, one or more incisions may be made into the patient proximal the relevant bony anatomy. Next, the handle 2030 (as assembled to stabilizing structure 2002, as shown in FIG. 48) may be used to position stabilizing structure 2002 proximate the relevant bony anatomy, such as the lateral side of the proximal femur. Next, the targeter 2034 may be assembled to the handle 2030 as shown in FIG. 49, although, in other embodiments, targeter 2034 may already have been assembled to handle 2030, or may not even be necessary. Subsequently, the drill sleeve 2038 may be inserted through targeter opening 2036 (although in other embodiments, drill sleeve 2038 may be associated directly with handle 2030 or may be associated with stabilizing structure 2002 in some other manner), as shown in FIG. 50.

As shown in FIGS. 51 and 52, a guide pin sleeve 2046 may be inserted into first tubular portion 2042. Next, a guide pin or wire may be inserted through a longitudinally extending aperture in guide pin sleeve 2046, and the guide pin or wire may engage a portion of the bony anatomy. In some embodiments, the axis of the guide pin may define the axis of the engaging member 2024, once the engaging member 2024 is installed. At this point, in some embodiments, fasteners may be installed through additional apertures 2008 to secure the stabilizing structure 2002 to the bony anatomy, although, in other embodiments, these fasteners may be installed at other points during the installation.

FIG. 53 shows the compression member drill guide 2048 being inserted into the second tubular portion 2044 of the drill sleeve 2038 next. An aperture extending through the compression member drill guide 2048 may receive a drill bit for preparing the bony anatomy to receive the compression member 2026. Subsequently, the compression member drill guide 2048 may be removed and a second drill bit may be guided through second tubular portion 2044 to prepare the bony anatomy to receive a portion of an insert 2010. In other embodiments, both of these drilling operations may be accomplished using a single combination drill bit, such as a bit similar to the combination drill bit described below. As shown in FIG. 55, an anti-rotation device 2050 may be subsequently inserted into second tubular portion 2044 such that a distal portion of the device 2050 fits into the portion of the bony anatomy prepared for the compression member 2026 and a proximal portion of the device 2050 fits into the portion of the bony anatomy prepared to receive a portion of the insert 2010.

Subsequently, the guide pin sleeve 2046 may be removed and one or more drill bits may be guided over the guide pin or wire through the first tubular portion 2042 to prepare the bony anatomy to receive the engaging member 2024 and other portions of the insert 2010. In some embodiments, this step may be accomplished using a combination drill bit that includes two different outer diameters. In other embodiments, multiple drill bits may be employed.

Next, the inserter 2052 shown in FIG. 56 may be used to install the engaging member 2024 and insert 2010, as described above and shown in FIGS. 56 through 60. Subsequently, the compression member 2026 may be installed. In some embodiments, the compression member 2026 may subsequently be used to compress the fracture, although in other embodiments, it may not be necessary or desirable to compress the fracture.

As those skilled in the art will appreciate, the particular embodiments of this invention described above and illustrated in the figures are provided for explaining the invention, and various alterations may be made in the structure and materials of the illustrated embodiments without departing from the spirit and scope of the invention as described above and in the following claims.

The invention claimed is:

1. A method for treating bone maladies, comprising:
    associating a stabilizing structure with an exterior of a first bone portion, the stabilizing structure comprising a first transverse aperture;
    engaging an engaging member with a second bone portion;
    at least partially inserting the engaging member through the first transverse aperture; and
    passing a compression member at least partially through the first transverse aperture;
    wherein the compression member at least indirectly interacts with the stabilizing structure;
    wherein the compression member contacts the second bone portion; and
    wherein the compression member contacts and interacts with an external surface of the engaging member to move the second bone portion towards the first bone portion.

2. The method for treating bone maladies of claim 1, further comprising using the compression member to facilitate a sliding movement of the engaging member with respect to the stabilizing structure, wherein the compression member at least indirectly interacts with the stabilizing structure to facilitate controlled movement between the first and second bone portions.

3. The method for treating bone maladies of claim 1, further comprising:
    associating a guide with the stabilizing structure; and
    using the guide to guide the movement of at least one bone preparation instrument.

4. The method for treating bone maladies of claim 3, wherein the guide is used to guide the movement of a plurality of bone preparation instruments.

5. The method for treating bone maladies of claim 3, wherein the guide is used to guide the movement of the at least one bone preparation instrument after the stabilizing structure has been associated with the first bone portion.

6. The method for treating bone maladies of claim 5, wherein the engaging member is engaged with the second bone portion after the stabilizing structure is associated with the first bone portion and after the guide is used to guide the movement of the at least one bone preparation instrument.

7. The method for treating bone maladies of claim 1, wherein the engaging member is at least partially inserted through the first transverse aperture after the engaging member is associated with the second bone portion.

8. The method for treating bone maladies of claim 2, wherein using the compression member to facilitate a sliding movement of the engaging member facilitates compressing the second bone portion with respect to the first bone portion.

9. The method for treating bone maladies of claim 1, wherein the engaging member comprises a channel and wherein the compression member at least partially nests within the channel.

10. The method for treating bone maladies of claim 9, wherein the engaging member comprises threads formed in the channel, and wherein the compression member interacts with the threads to move the second bone portion towards the first bone portion.

11. A method for treating bone maladies, comprising:
    associating a stabilizing structure with an exterior of a first bone portion, the stabilizing structure comprising a transverse aperture;
    engaging an engaging member with a second bone portion, the engaging member comprising an exterior channel and a cooperation structure located in the channel;
    at least partially inserting the engaging member through the transverse aperture; and
    passing a compression member at least partially through the transverse aperture;
    wherein the compression member at least indirectly interacts with the stabilizing structure; and
    wherein the compression member at least partially nests within the channel and interacts with the cooperation structure of the engaging member to move the second bone portion towards the first bone portion.

12. The method for treating bone maladies of claim 11, wherein the cooperation structure comprises threads, and further comprising rotating the compression member to move the second bone portion towards the first bone portion.

13. The method for treating bone maladies of claim 11, wherein the engaging member is at least partially inserted through the transverse aperture after the engaging member is engaged with the second bone portion.

* * * * *

UNITED STATES PATENT AND TRADEMARK OFFICE
CERTIFICATE OF CORRECTION

PATENT NO. : 7,799,030 B2
APPLICATION NO. : 11/725872
DATED : September 21, 2010
INVENTOR(S) : Kohsuke Watanabe et al.

It is certified that error appears in the above-identified patent and that said Letters Patent is hereby corrected as shown below:

On the title page, item [56]: Column 2 (Other Publications), Line 1, delete "(tantum)))", and insert -- (tantum) --;

Column 7, Line 46, after "24", insert -- . --;

Column 16, Line 12, delete "lag-screw", and insert -- lag screw --.

Signed and Sealed this

Thirtieth Day of November, 2010

David J. Kappos
*Director of the United States Patent and Trademark Office*